US012630544B2

(12) United States Patent
Higuchi et al.

(10) Patent No.: US 12,630,544 B2
(45) Date of Patent: May 19, 2026

(54) COMPOUND, α-SYNUCLEIN AGGREGATE BINDER, AND USE THEREOF

(71) Applicants: NATIONAL INSTITUTES FOR QUANTUM SCIENCE AND TECHNOLOGY, Chiba (JP); Eisai R&D Management Co., Ltd., Tokyo (JP); Ono Pharmaceutical Co., Ltd., Osaka (JP); TAKEDA PHARMACEUTICAL COMPANY LIMITED, Osaka (JP)

(72) Inventors: Makoto Higuchi, Chiba (JP); Maiko Ono, Chiba (JP); Meiei Cho, Chiba (JP); Takeshi Yamamoto, Fujisawa (JP); Takeshi Wakabayashi, Fujisawa (JP)

(73) Assignees: NATIONAL INSTITUTES FOR QUANTUM SCIENCE AND TECHNOLOGY, Chiba (JP); Eisai R&D Management Co., Ltd., Tokyo (JP); Ono Pharmaceutical Co., Ltd., Osaka (JP); TAKEDA PHARMACEUTICAL COMPANY LIMITED, Osaka (JP)

( * ) Notice: Subject to any disclaimer, the term of this patent is extended or adjusted under 35 U.S.C. 154(b) by 730 days.

(21) Appl. No.: 18/022,800

(22) PCT Filed: Aug. 24, 2021

(86) PCT No.: PCT/JP2021/030899
§ 371 (c)(1),
(2) Date: Jun. 9, 2023

(87) PCT Pub. No.: WO2022/045093
PCT Pub. Date: Mar. 3, 2022

(65) Prior Publication Data

US 2023/0399323 A1 Dec. 14, 2023

(30) Foreign Application Priority Data

Aug. 25, 2020 (JP) ................................. 2020-142080

(51) Int. Cl.
*C07D 417/06* (2006.01)
*A61K 49/00* (2006.01)
*A61K 51/04* (2006.01)

(52) U.S. Cl.
CPC ........ *C07D 417/06* (2013.01); *A61K 49/0021* (2013.01); *A61K 51/0459* (2013.01)

(58) Field of Classification Search
CPC . A61K 49/0021; A61K 31/506; A61K 31/497
See application file for complete search history.

(56) References Cited

U.S. PATENT DOCUMENTS

| | | | |
|---|---|---|---|
| 2015/0239878 A1 | 8/2015 | Higuchi et al. |
| 2019/0071450 A1 | 3/2019 | Molette et al. |
| 2022/0133698 A1 | 5/2022 | Higuchi et al. |
| 2023/0039932 A1 | 2/2023 | Booij et al. |

FOREIGN PATENT DOCUMENTS

| | | | |
|---|---|---|---|
| CN | 113490494 A | 10/2021 |
| EP | 2767532 A1 | 8/2014 |
| JP | 2019-512491 A | 5/2019 |
| WO | 2014/097474 A1 | 6/2014 |
| WO | 2018/138088 A1 | 8/2018 |
| WO | 2018/234864 A2 | 12/2018 |
| WO | 2019/121661 A1 | 6/2019 |
| WO | 2019/138296 A2 | 7/2019 |
| WO | 2019/222454 A1 | 11/2019 |
| WO | 2020/174963 A1 | 9/2020 |
| WO | 2022/045093 A1 | 3/2022 |

OTHER PUBLICATIONS

Koga et al., Fluorescence and autoradiographic evaluation of tau PET ligand PBB3 to alpha-synuclein pathology. Mov Disord. Jun. 2017;32(6):884-892.
European Office Action for Application No. 21861518.5, dated Jul. 29, 2024, 6 pages.
Miranda-Azpiazu et al., Identification and in vitro characterization of C05-01, a PBB3 derivative with improved affinity for alpha-synuclein. Brain Res. Dec. 15, 2020;1749:147131, 9 pages.
U.S. Appl. No. 18/841,267, filed Aug. 23, 2024, Pending.
Chinese Office Action for Application No. 202180052639.2, dated Dec. 26, 2024, 12 pages.

(Continued)

*Primary Examiner* — James W Rogers
(74) *Attorney, Agent, or Firm* — McCarter & English, LLP

(57) ABSTRACT

An embodiment of the present invention relates to a compound represented by formula (I) or (II), a pharmaceutically acceptable salt thereof, or a solvate thereof.

(I)

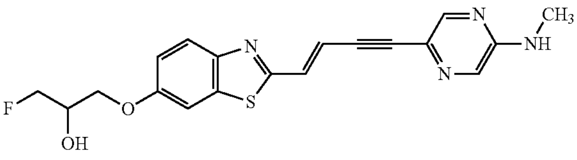

(II)

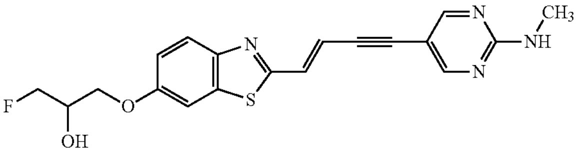

10 Claims, 11 Drawing Sheets

(56) References Cited

OTHER PUBLICATIONS

Kikuchi et al., In vivo visualization of a-synuclein deposition by carbon-11-labelled 2-[2-(2-dimethylaminothiazol-5-yl) ethenyl]-6-[2-(fluoro)ethoxy]benzoxazole positron emission tomography in multiple system atrophy. Brain. Jun. 2010;133(6):1772-8.
Masuda-Suzukake et al., Pathological alpha-synuclein propagates through neural networks. Acta Neuropathol Commun. Aug. 6, 2014;2:88.
Shimozawa et al., Propagation of pathological a-synuclein in marmoset brain. Acta Neuropathol Commun. Feb. 2, 2017;5(1):12.
Tomita et al., Long-term in vivo investigation of mouse cerebral microcirculation by fluorescence confocal microscopy in the area of focal ischemia. J Cereb Blood Flow Metab. Jul. 2005;25(7):858-67.
Verdurand et al., Amyloid-Beta Radiotracer [18F]BF-227 Does Not Bind to Cytoplasmic Glial Inclusions of Postmortem Multiple System Atrophy Brain Tissue. Contrast Media Mol Imaging. Feb. 6, 2018;2018:8 pages.
International Search Report and Written Opinion for Application No. PCT/JP2021/030899, dated Sep. 28, 2021, 5 pages.

(a)

Staining with use of anti-phosphorylated α-synuclein antibody

Fluorescent staining by SPAL-T-06

(b)

Staining with use of anti-phosphorylated α-synuclein antibody

Fluorescent staining by SPAL-T-06

COMPOUND, α-SYNUCLEIN AGGREGATE BINDER, AND USE THEREOF

CROSS REFERENCE TO RELATED APPLICATIONS

This application is a U.S. National Stage Application filed under 35 U.S.C. § 371, based on International Patent Application No. PCT/JP2021/030899, filed on Aug. 24, 2021, which claims priority to JP Patent Application No. 2020-142080, filed on Aug. 25, 2020. The entire contents of the above-referenced applications are incorporated herein by reference.

TECHNICAL FIELD

The present invention relates to a novel compound, an α-synuclein aggregate binding agent, and use thereof, specifically, relates to a novel compound, an α-synuclein aggregate binding agent containing the novel compound, a composition for optical imaging of α-synuclein aggregates, a composition for radiological imaging of α-synuclein aggregates, a method for carrying out optical imaging of α-synuclein aggregates in brain, a method for carrying out radiological imaging of α-synuclein aggregates in brain, and an intermediate for synthesizing the novel compound.

BACKGROUND ART

It has been considered that α-synuclein aggregates form a core pathology of Parkinson's disease, dementia with Lewy bodies (DLB), and multiple system atrophy (MSA) and have a close causal association with neurodegeneration. Definitive diagnoses of these diseases are carried out while the presence of α-synuclein aggregates (also referred to as "α-synuclein lesion" herein) is used as an indicator in a pathological examination of the autopsied brain and therefore, it is impossible to make a definitive diagnosis while a patient is alive. However, if α-synuclein aggregates can be visualized in the living brain, it is possible to obtain information close to definitive information concerning diagnoses of these diseases (definitive diagnosis) from an early stage. Moreover, if α-synuclein aggregates can be visualized in the brain of a living disease model animal, such visualization can also help assess the efficacy of a candidate substance for a therapeutic or preventive agent targeting the α-synuclein aggregates, by imaging over time and the like.

[$^{11}$C]BF-227 is an example of a positron emission tomography (PET) probe that has previously shown to bind to α-synuclein in the living brain (Non-Patent Literatures 1 and 2). However, [$^{11}$C]BF-227 has insufficient binding affinity with respect to the α-synuclein aggregates, and α-synuclein lesions can be detected only in a subset of patients with MSA among the above diseases. In addition, [$^{11}$C]BF-227 has a problem of nonspecific accumulation in the brain and a problem of low binding selectivity with respect to the α-synuclein aggregates because [$^{11}$C]BF-227 binds to amyloid-β aggregates.

The inventors developed a compound for imaging a tau protein accumulated in the brain (see Patent Literature 1). The compound described in Patent Literature 1 allows imaging of a tau protein accumulated in the brain, and therefore the technology of Patent Literature 1 is useful for treatment, prevention, and the like of a disease (e.g., Alzheimer's disease (AD)) caused by accumulation of a tau protein. However, Patent Literature 1 does not describe the compound's binding to the α-synuclein aggregates.

CITATION LIST

Patent Literature

[Patent Literature 1]
International Publication No. WO 2014/097474, pamphlet

Non-Patent Literature

[Non-patent Literature 1]
Kikuchi, A. et al., Brain, 133:1772-1778 (2010)
[Non-patent Literature 2]
Verdurand, M. et al., Contrast Media Mol. Imaging, 2018: 9165458 (2018)

SUMMARY OF INVENTION

Technical Problem

The present invention has been accomplished in view of the above circumstances, and its objective is to provide an α-synuclein aggregate binding agent having high binding selectivity with respect to α-synuclein aggregates, a method for carrying out imaging with use of the α-synuclein aggregate binding agent, and a novel compound which can be used for an α-synuclein aggregate binding agent.

Solution to Problem

The inventors of the present invention found that a compound having a specific structure has high binding selectivity with respect to α-synuclein aggregates, and conducted further studies to complete the present invention. More specifically, the present invention provides the following features.

An aspect of the present invention is a compound represented by the following formula (I) or (II), a pharmaceutically acceptable salt thereof, or a solvate thereof.

(I)

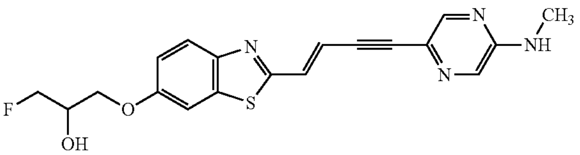

(II)

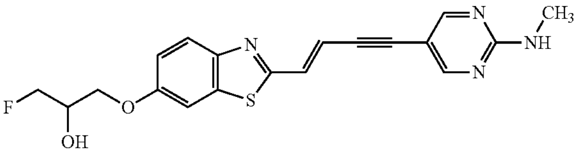

Advantageous Effects of Invention

According to the present invention, it is possible to provide an α-synuclein aggregate binding agent having high binding selectivity with respect to α-synuclein aggregates.

DESCRIPTION OF EMBODIMENTS

Figure 1:
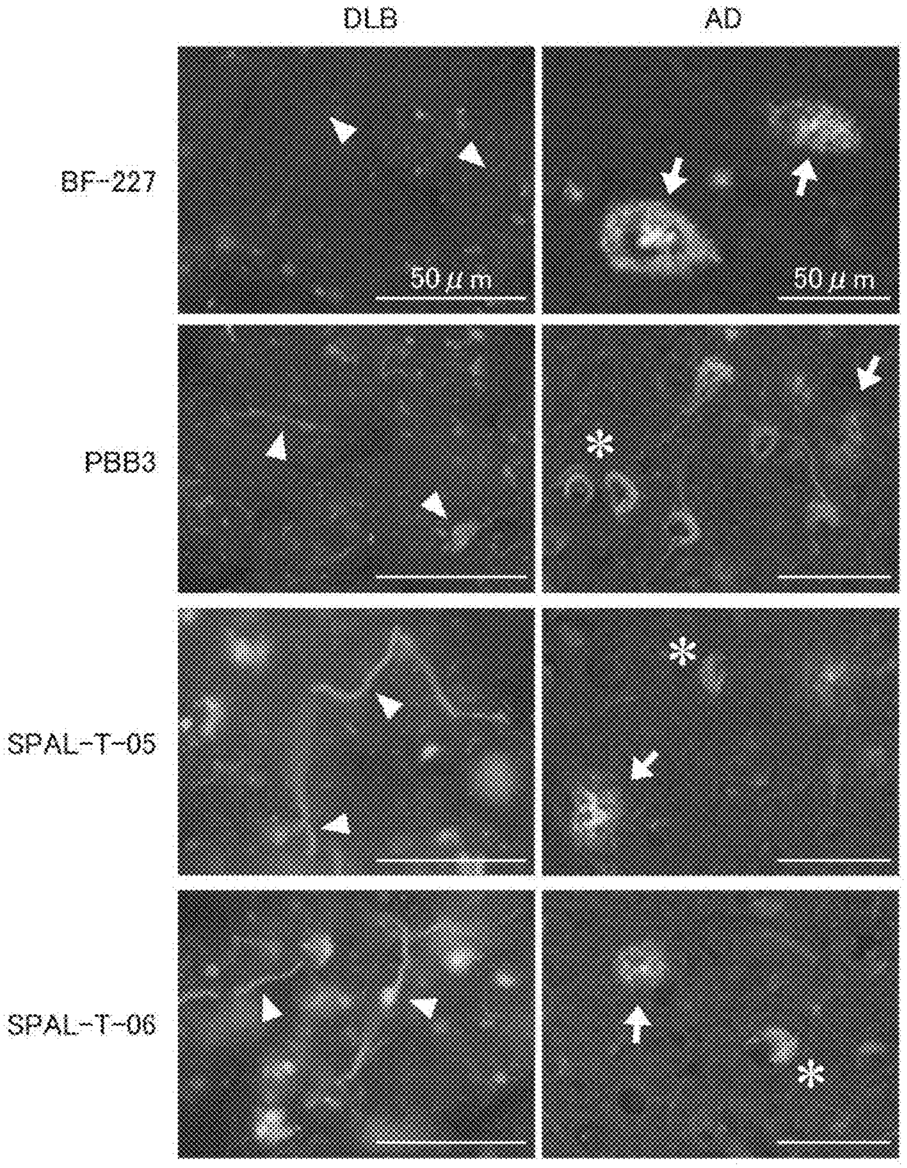
FIG. 1 is a diagram showing results of fluorescence microscope measurement of the brains of DLB and AD patients.

The following description describes embodiments of the present invention. Note that, as used herein, the expression "A and/or B" is intended to mean at least one of A and B.

[Definition]

The term "pharmaceutically acceptable salt" refers to a salt that is not harmful to mammals, particularly to humans. The pharmaceutically acceptable salt can be formed with use of a non-toxic acid or base. The non-toxic acid includes inorganic acids and organic acids, and the non-toxic base includes inorganic bases and organic bases. Examples of the pharmaceutically acceptable salt include: metal salts formed from aluminum, calcium, lithium, magnesium, potassium, sodium, zinc, and the like; and organic salts formed from lysine, N,N'-dibenzylethylenediamine, chloroprocaine, choline, diethanolamine, ethylenediamine, meglumine (N-methylglucamine), procaine, and the like. The pharmaceutically acceptable salt also includes acid-addition salts and base-addition salts.

The term "pharmaceutically acceptable carrier" means a pharmaceutically acceptable material, composition, or vehicle, such as a physiological saline solution, a liquid or solid filler, a diluent, a solvent, or an encapsulant. Examples of the pharmaceutically acceptable carrier include water, saline, physiological saline, phosphate buffered saline (PBS), sodium chloride injection solutions, Ringer's injection solutions, isotonic dextrose injection solutions, sterile water injection solutions, dextrose, and lactated Ringer's injection solutions.

The term "effective amount" refers to the amount of a compound or a composition which amount makes it possible to bring about an intended effect. For example, in some aspects, the effective amount refers to the amount of a compound or a composition which amount enables optical or radiological imaging of a substance (such as α-synuclein aggregates) accumulated in the brain.

The term "solvate" means a solvent-containing compound that is formed by association of one or more solvent molecules to a compound. Examples of the solvate include monosolvates, disolvates, trisolvates, and tetrasolvates. The solvate also includes hydrates.

The term "hydrate" means a compound that further contains a stoichiometric or a non-stoichiometric amount of water constrained by a non-covalent bonding intermolecular force, or a salt thereof. Examples of the hydrate include monohydrates, dihydrates, trihydrates, and tetrahydrates.

The term "treatment" means moderating or remitting progress, the severity, and/or a duration of a disease or condition.

The term "prevention" means reducing a risk of catching or progressing a given disease or condition, or reducing or inhibiting relapse, onset, or progress of one or more symptoms of a given disease or condition.

The term "binding performance" means strength with which a compound binds to specific protein aggregates.

The term "binding selectivity" indicates that, when compared, the binding performance of a compound with respect to specific protein aggregates and the binding performance of the compound with respect to other protein aggregates differ from each other (the binding performance with respect to the specific protein aggregates is higher or lower than the binding performance with respect to the other protein aggregates). The phrase "high binding selectivity" means that the above difference in binding performance is large. For example, that a compound has "high binding selectivity with respect to α-synuclein aggregates" indicates that there is a large difference between the binding performance of the compound with respect to the α-synuclein aggregates and the binding performance of the compound with respect to other protein aggregates and the compound has higher binding performance with respect to the α-synuclein aggregates.

[Compound]

In an embodiment, the present invention provides (E)-1-fluoro-3-((2-(4-(5-(methylamino)pyrazin-2-yl)but-1-en-3-yn-1-yl)benzo[d]thiazol-6-yl)oxy)propan-2-ol, which is represented by the following structural formula (I), or (E)-1-fluoro-3-((2-(4-(2-(methylamino)pyrimidin-5-yl)but-1-en-3-yn-1-yl)benzo[d]thiazol-6-yl)oxy)propan-2-ol, which is represented by the following structural formula (II), a pharmaceutically acceptable salt thereof, or a solvate thereof.

(I)

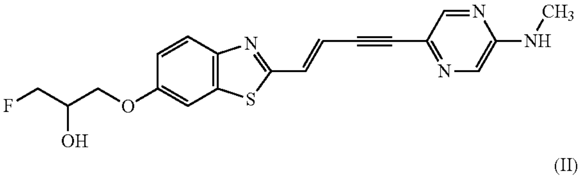

(II)

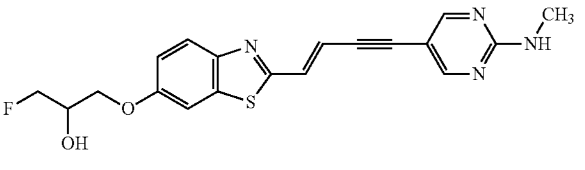

Herein, the compounds represented by formulae (I) and (II) will be also referred to as "compound (I)" and "compound (II)", respectively.

In an aspect, the compound (I) and the compound (II) are each a compound in which at least one atom is a radioisotope thereof, a salt thereof, or a solvate thereof. The radioisotope is selected from the group consisting of $^{15}O$, $^{13}N$, $^{11}C$, $^{18}F$, and the like, but is not particularly limited. Preferably, the radioisotope is $^{11}C$ or $^{18}F$. Among these, in consideration of the fact that the half-life of $^{11}C$ is approximately 20 minutes and the half-life of $^{18}F$ is approximately 110 minutes, a compound that is labeled with $^{18}F$ would be commercially more useful. Therefore, the radioisotope is most preferably $^{18}F$.

Preferably, at least one of a methylamino group binding to a pyrimidine ring or a pyrazine ring and a 3-fluoro-2-hydroxypropoxy group ($—O—CH_2—CH(OH)—CH_2F$) binding to a benzothiazole ring is a group containing a radioisotope. More preferably, the 3-fluoro-2-hydroxypropoxy group binding to the benzothiazole ring is a group containing a radioisotope. Still more preferably, a fluorine atom in the 3-fluoro-2-hydroxypropoxy group is a radioisotope.

In an aspect, the compound (I) which contains a radioisotope is preferably [$^{18}F$]-(E)-1-fluoro-3-((2-(4-(5-(methylamino) pyrazin-2-yl) but-1-en-3-yn-1-yl)benzo[d]thiazol-6-yl)oxy)propan-2-ol.

In an aspect, the compound (II) which contains a radioisotope is preferably [$^{18}F$]-(E)-1-fluoro-3-((2-(4-(2-(methylamino)pyrimidin-5-yl)but-1-en-3-yn-1-yl)benzo[d]thiazol-6-yl)oxy)propan-2-ol.

[Intermediate]

As shown in a method for producing the compound below, a compound represented by the following formula (III) is an intermediate compound (herein, simply referred to as "intermediate") produced during production of the compound (I) and the compound (II).

(III)

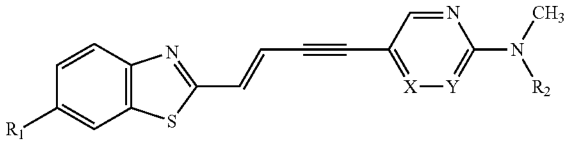

In formula (III), one of X and Y is a nitrogen atom, and the other is an unsubstituted carbon atom. The term "unsubstituted carbon atom" herein indicates CH. That is, in formula (III), in a case where X is a nitrogen atom (N), Y is an unsubstituted carbon atom (CH), whereas in a case where X is an unsubstituted carbon atom (CH), Y is a nitrogen atom (N).

$R_1$ is a hydroxy group or a group represented by the following formula (i).

(i)

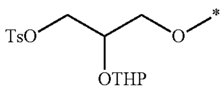

Here, Ts represents a p-toluenesulfonyl group, THP represents a tetrahydro-2H-pyran-2-yl group, and * represents a position to which the benzothiazole ring binds.

$R_2$ is a hydrogen atom or a tert-butoxycarbonyl (Boc) group.

These intermediate compounds are suitably used to synthesize the compound (I) and the compound (II), and further used to synthesize the compound (I) and the compound (II) each of which is labeled with a radioisotope. These intermediate compounds may be salts.

In a case where the compound (I) or the compound (II) has any of various isomers such as stereoisomers (including optical isomers and rotamers), tautomers, and polar isomers, such an isomer is also included in the compound (I) or the compound (II). These isomers can be each obtained as a single isomer, by a known synthesizing method or a separating method. The compound (III) can also include various isomers.

The compound (I), the compound (II), or the compound (III) may be a crystal produced by a known crystallizing method.

[Method for Producing Compound (I), Compound (II), and Intermediate]

The compound (I), the compound (II), and the compound (III), which is an intermediate, can be produced in accordance with a method based on a production method below. As desired, the compound (I), the compound (II), and the compound (III) can be produced by carrying out one or a combination of two or more of a deprotection reaction, an amidation reaction, a ureation reaction, an alkylation reaction, a Mitsunobu reaction, an oxidation reaction, a reduction reaction, a halogenation reaction, a coupling reaction, a nucleophilic addition reaction by a carbanion, a Grignard reaction, a dehydration reaction, and the like. Conditions, such as a solvent, a reagent, and a temperature, of each reaction can be set as appropriate, on the basis of the common technical knowledge of a person skilled in the art. A protection reaction and a deprotection reaction of a functional group are each carried out in accordance with a known reaction method or a method described in Reference Examples or Examples. As a protecting group, a conventional group is used.

Each symbol used in the following production method has the same meaning as the above-described symbol, unless otherwise specified.

(Production Method A)

The compound (I), the compound (II), and the compound (III) in which $R_1$ is a hydroxy group and $R_2$ is a Boc group (compound (III-i)) can be produced by a method shown in Production Scheme 1 below. In the following description, compounds represented by (1), (2), and the like in schemes below will be referred to as a compound (1), a compound (2), and the like, respectively.

(Production Scheme 1)

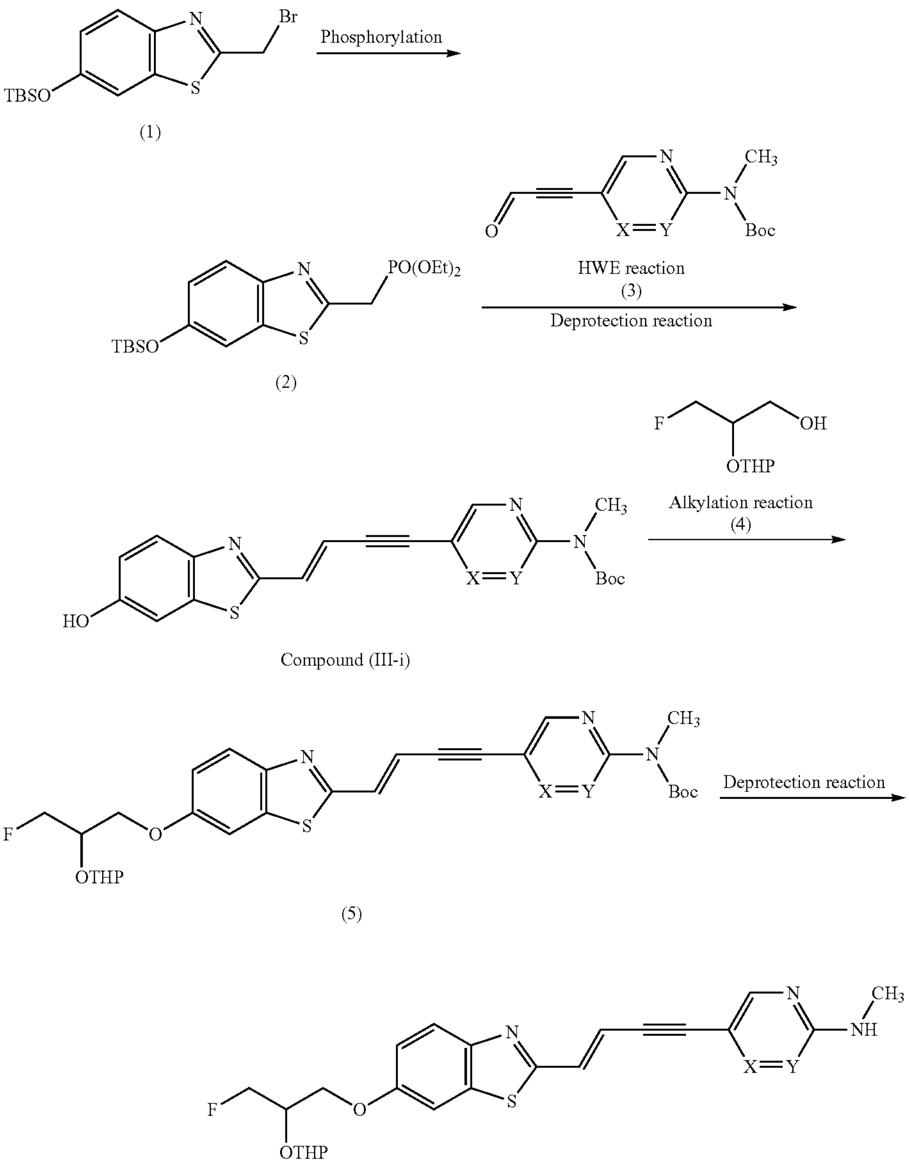

(1)

(3)

(2)

(4)

Compound (III-i)

(5)

Compound (I): X is N, and Y is CH.
Compound (II): X is CH, and Y is N,

A compound (2) can be produced by a reaction between a compound (1) and phosphite triester. In the compound (1), TBS represents a tert-butyldimethylsilyl group.

The compound (III-i) can be produced by a Horner-Wadsworth-Emmons reaction (HWE reaction) between the compound (2) and a compound (3) (described later) and a deprotection reaction which progresses during the reaction. In the compound (3), one of X and Y is a nitrogen atom, and the other is an unsubstituted carbon atom (CH).

A compound (5) can be produced by an alkylation reaction, such as a Mitsunobu reaction, between the compound (III-i) and a compound (4) (described later).

The compound (I) and the compound (II) can be produced by a deprotection reaction of the compound (5).

The compound (3) used in Production Method A can be produced from a compound (6) by a method shown in Production Scheme 2 below.

(Production Scheme 2)

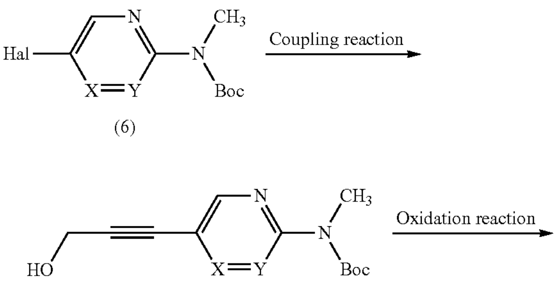

(6)

(7)

-continued

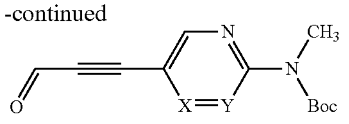

(3)

In the compound (6), Hal represents a halogen atom (e.g. a chlorine atom, a bromine atom, or a iodine atom). A compound (7) can be produced by a coupling reaction or the like between the compound (6) and 2-propyn-1-ol.

The compound (3) can be produced by an oxidation reaction of a compound (7).

The compound (4) used in Production Method A can be produced from a compound (8) by a method shown in Production Scheme 3 below.

(Production Scheme 3)

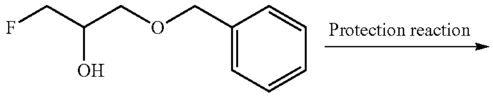

(8)

-continued

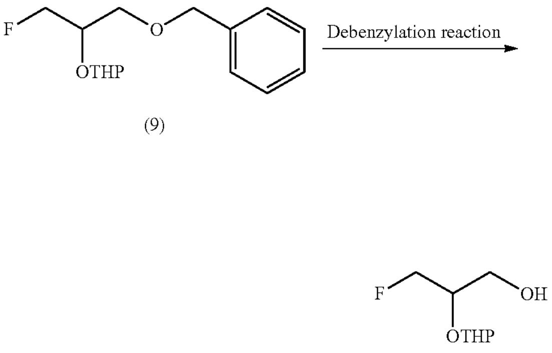

(9)

(4)

A compound (9) can be produced by a protection reaction of the compound (8).

The compound (4) can be produced by a debenzylation reaction of the compound (9).

The compound (5) used in Production Method A can be also produced from the compound (2) by a method shown in Production Scheme 4 below.

(Production Scheme 4)

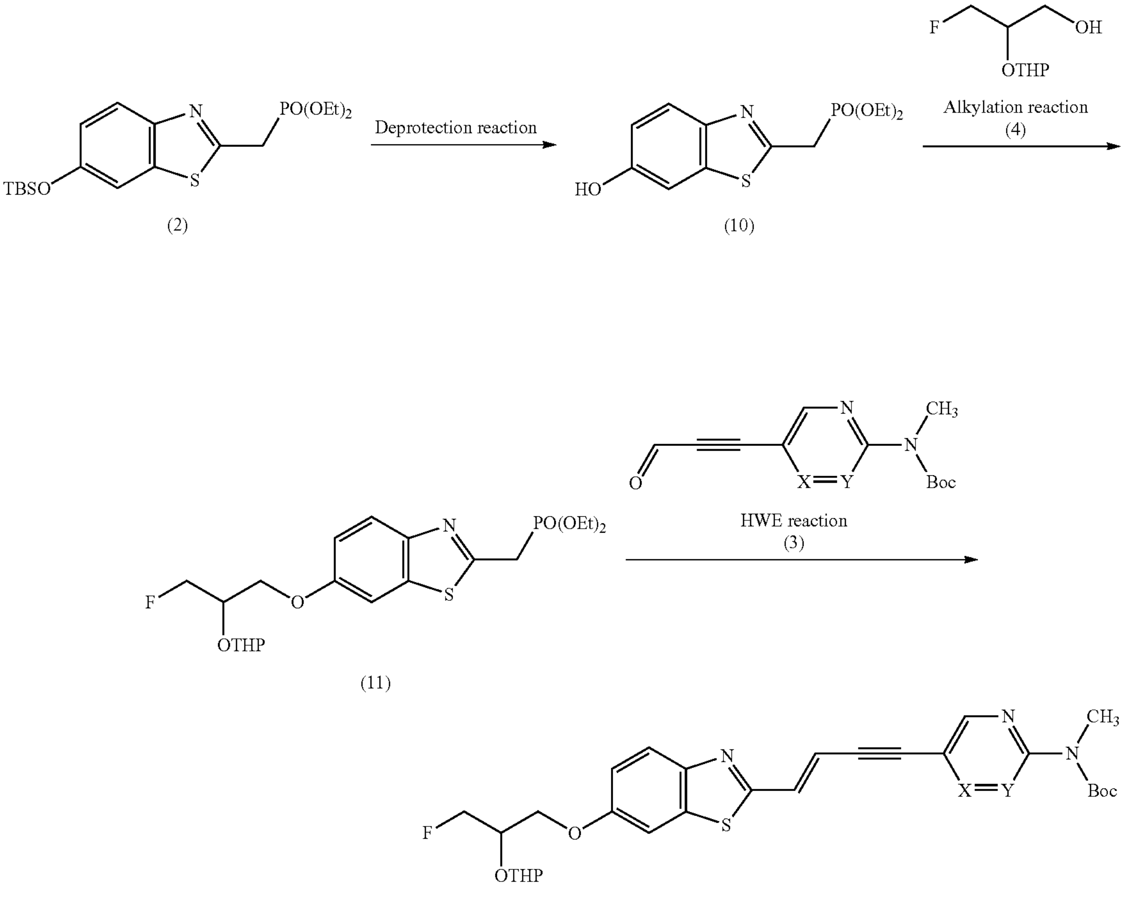

(2)

(10)

(11)

(5)

A compound (10) can be produced by a deprotection reaction of the compound (2).

A compound (11) can be produced by an alkylation reaction, such as a Mitsunobu reaction, between the compound (10) and the compound (4).

The compound (5) can be also produced by an HWE reaction between the compound (11) and the compound (3).

(Production Method B)

The compound (I) and the compound (II) can be also produced by a method shown in Production Scheme 5 below.

(Production Scheme 5)

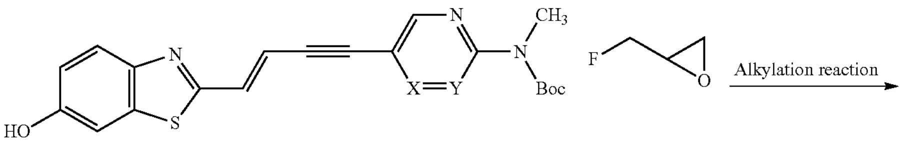

Compound (III-i) (12)

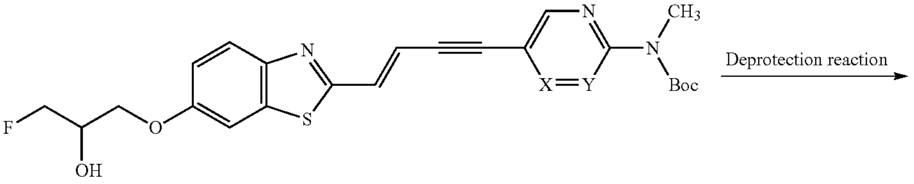

(13)

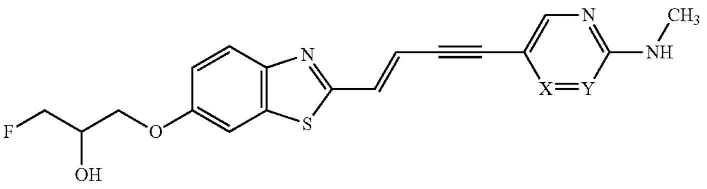

Compound (I): X is N, and Y is CH,
Compound (II): X is CH, and Y is N,

A compound (13) can be produced by an alkylation reaction of the compound (III-i) involving an oxirane ring-opening reaction of the compound (12).

The compound (I) and the compound (II) can be produced by a deprotection reaction of the compound (13).

(Production Method C)

The compound (III) in which $R_1$ is a hydroxy group and $R_2$ is a hydrogen atom (compound (III-ii)) can be produced by a deprotection reaction of the compound (III-i), as shown in Production Scheme 6 below.

(Production Scheme 6)

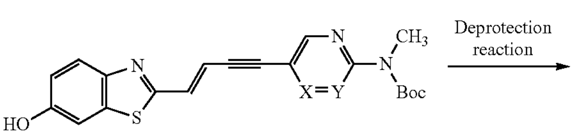

Compound (III-i)

-continued

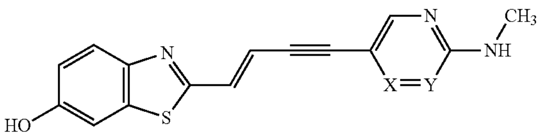

Compound (III-ii)

(Production Method D)

The compound (III) in which $R_1$ is a group represented by formula (i) (compound (III-iii)) can be produced by a method shown in Production Scheme 7 below.

(Production Scheme 7)

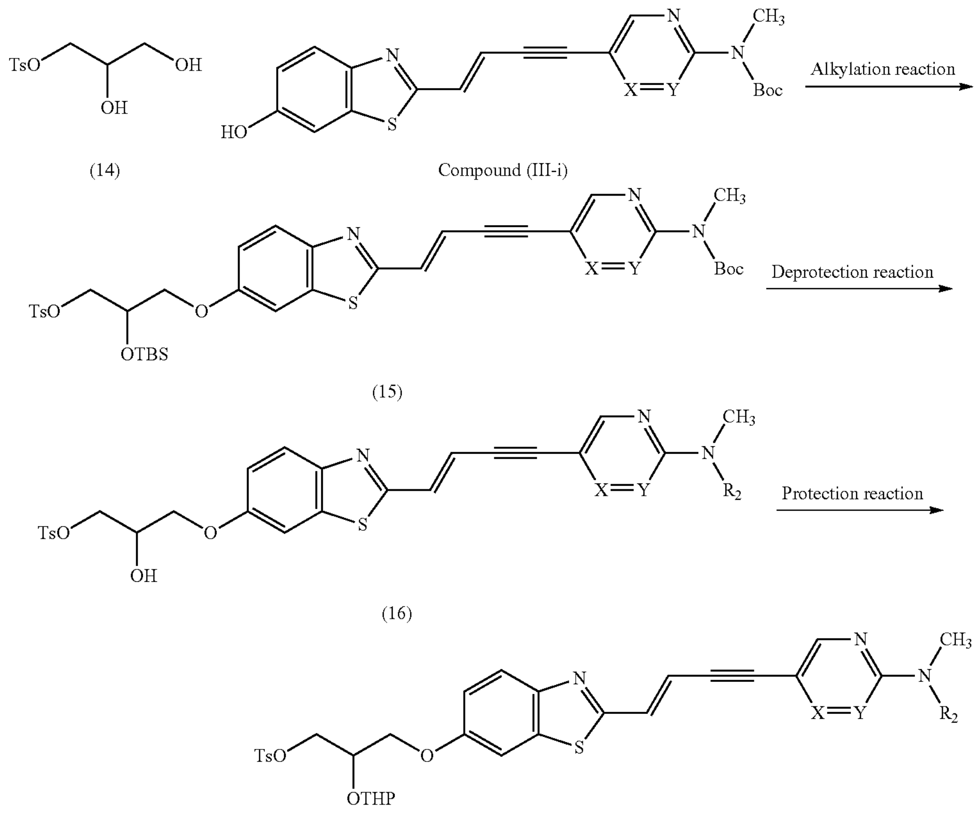

(14)

Compound (III-i)

(15)

(16)

Compound (III-iii)

A compound (15) can be produced by an alkylation reaction, such as a Mitsunobu reaction, between the compound (III-i) and a compound (14) (described later).

A compound (16) can be produced by a deprotection reaction of the compound (15).

The compound (III-iii) can be produced by a protection reaction of the compound (16).

The compound (14) used in Production Method D can be produced by a method shown in Production Scheme 8 below.

(Production Scheme 8)

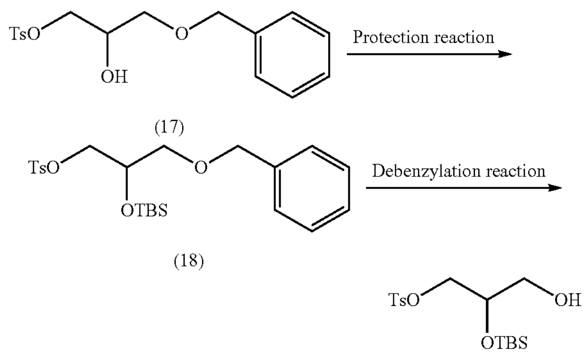

(17)

(18)

(14)

A compound (18) can be produced by a protection reaction of a compound (17).

The compound (14) can be produced by a debenzylation reaction of the compound (18).

[α-Synuclein Aggregate Binding Agent]

In an embodiment, the present invention provides an α-synuclein aggregate binding agent. The α-synuclein aggregate binding agent (hereinafter also referred to as "binding agent" or "α-synuclein aggregate binding agent") in accordance with the present embodiment contains a compound (I) or a compound (II), a pharmaceutically acceptable salt thereof, or a solvate thereof.

The compound (I) and the compound (II) each have higher binding selectivity with respect to α-synuclein aggregates than with respect to aggregates of a tau protein and aggregates of an amyloid-β peptide. Similarly, the pharmaceutically acceptable salt of each of the compound (I) and the compound (II) and the solvate of each of the compound (I) and the compound (II) have higher binding selectivity with respect to α-synuclein aggregates than with respect to aggregates of a tau protein and aggregates of an amyloid-β peptide. The compound (I) and the compound (II) each fluoresce. Further, as described above, in each of the compound (I) and the compound (II), at least one atom can be a radioisotope thereof. Therefore, the binding agent in accordance with the present embodiment can be used as a molecular probe for optical imaging or radiological imaging of α-synuclein aggregates accumulated in the brain.

Note that α-synuclein is a protein that localizes at a neuronal synapse also in the normal brain, and α-synuclein aggregates to form α-synuclein aggregates.

The α-synuclein aggregate binding agent can contain a pharmaceutically acceptable carrier. Examples of the pharmaceutically acceptable carrier include water, saline, physiological saline, phosphate buffered saline (PBS), sodium chloride injection solutions, Ringer's injection solutions, isotonic dextrose injection solutions, sterile water injection solutions, dextrose, and lactated Ringer's injection solutions.

The amounts of the compound (I) or the compound (II), a pharmaceutically acceptable salt thereof, or a solvate thereof and the pharmaceutically acceptable carrier contained in the α-synuclein aggregate binding agent are not particularly limited. These amounts are determined based on various factors such as: the compound to be used: the age, weight, health conditions, sex, and diet of a mammal to which administration is carried out; the number of times of administration and the route of the administration; the period of treatment; and other drugs that are concurrently used. The amount of the pharmaceutically acceptable carrier can be 1% by weight to 99% by weight of the α-synuclein aggregate binding agent. The α-synuclein aggregate binding agent is prepared such that, for example, the compound (I) or the compound (II) can be administered in an amount of 5 ng/kg to 5 mg/kg per weight (kg) of a subject. Preferably, the lower limit of the amount of the compound (I) or the compound (II) is not less than 5 ng/kg, not less than 0.01 mg/kg, not less than 0.05 mg/kg, or not less than 0.1 mg/kg. The upper limit of the amount of the compound (I) or the compound (II) is not more than 5 mg/kg, not more than 3 mg/kg, not more than 1 mg/kg, or not more than 20 μg/kg.

[Composition for Optical Imaging of α-Synuclein Aggregates]

In an embodiment, the present invention provides a composition for optical imaging of α-synuclein aggregates. The composition for optical imaging of α-synuclein aggregates in accordance with the present embodiment (hereinafter also referred to as "composition for optical imaging") contains the above-described binding agent in accordance with the present embodiment. The optical imaging encompasses in vitro, ex vivo, and in vivo imaging.

Examples of the optical imaging include fluorescence microscope measurement, multiphoton imaging, two-photon imaging, and near infrared fluorescence imaging.

The composition for optical imaging can contain a pharmaceutically acceptable carrier. Examples of the pharmaceutically acceptable carrier include water, saline, physiological saline, phosphate buffered saline (PBS), sodium chloride injection solutions, Ringer's injection solutions, isotonic dextrose injection solutions, sterile water injection solutions, dextrose, and lactated Ringer's injection solutions.

The amounts of the compound (I) or the compound (II), a pharmaceutically acceptable salt thereof, or a solvate thereof and the pharmaceutically acceptable carrier contained in the composition for optical imaging are not particularly limited. These amounts are determined based on various factors such as: the compound to be used: the age, weight, health conditions, sex, and diet of a mammal to which administration is carried out; the number of times of administration and the route of the administration; the period of treatment; and other drugs that are concurrently used. The amount of the pharmaceutically acceptable carrier can be 1% by weight to 99% by weight of the composition for optical imaging. The composition for optical imaging is prepared such that, for example, the compound (I) or the compound (II) can be administered in an amount (mg) of 0.01 mg/kg to 5 mg/kg, preferably 0.05 mg/kg to 3 mg/kg, and still more preferably 0.1 mg/kg to 1 mg/kg, per weight (kg) of a subject.

[Composition for Radiological Imaging of α-Synuclein Aggregates]

In an embodiment, the present invention provides a composition for radiological imaging of α-synuclein aggregates. The composition for radiological imaging of α-synuclein aggregates in accordance with the present embodiment (hereinafter also referred to as "composition for radiological imaging") contains the above-described binding agent in accordance with the present embodiment. The radiological imaging encompasses in vitro, ex vivo, and in vivo imaging.

Examples of the radiological imaging include positron emission tomography (PET), single-photon emission computed tomography (SPECT), and autoradiography.

The composition for radiological imaging can contain a pharmaceutically acceptable carrier. Examples of the pharmaceutically acceptable carrier include water, saline, physiological saline, phosphate buffered saline (PBS), sodium chloride injection solutions, Ringer's injection solutions, isotonic dextrose injection solutions, sterile water injection solutions, dextrose, and lactated Ringer's injection solutions.

The amounts of the compound (I) or the compound (II), a pharmaceutically acceptable salt thereof, or a solvate thereof and the pharmaceutically acceptable carrier contained in the composition for radiological imaging are not particularly limited. These amounts are determined based on various factors such as: the compound to be used: the age, weight, health conditions, sex, and diet of a mammal to which administration is carried out; the number of times of administration and the route of the administration; the period of treatment; and other drugs that are concurrently used. The amount of the pharmaceutically acceptable carrier can be 1% by weight to 99% by weight of the composition for radiological imaging. The composition for radiological imaging is prepared such that, for example, the compound (I) or the compound (II) can be administered in an amount of 5 ng/kg to 5 mg/kg and preferably 5 ng/kg to 20 μg/kg per weight (kg) of a subject.

[Diagnostic agent for diseases associated with α-synuclein aggregates or companion diagnostic agent for treating or preventing those diseases]

In an embodiment, the present invention provides a diagnostic agent for diseases associated with α-synuclein aggregates or a companion diagnostic agent for treating or preventing the diseases. The diagnostic agent for diseases associated with α-synuclein aggregates or the companion diagnostic agent for treating or preventing the diseases (hereinafter also referred to "companion diagnostic agent") in accordance with the present embodiment contains the above-described binding agent in accordance with the present embodiment. The companion diagnostic agent for treatment is a diagnostic agent for, when a disease is found, determining whether treatment would be possible or not. The companion diagnostic agent for prevention is a diagnostic agent for, when a precursor state of a diseases is found, predicting the future onset or determining whether prevention for suppressing the onset would be possible or not.

By collating the amount and/or distribution of α-synuclein aggregates in the brain of a subject, which is obtained by using the diagnostic agent of the present embodiment, with previously-obtained correlation between a disease and the amount and/or distribution of α-synuclein aggregates, it is possible to diagnose the condition of the disease in the subject (specifically, the presence or absence of the disease, the severity of the disease, the possibility of having episode, and the like).

Moreover, by collating the amount and/or distribution of α-synuclein aggregates in the brain of a subject, which is obtained by using the companion diagnostic agent of the present embodiment, with previously-obtained correlation between a disease and the amount and/or distribution of α-synuclein aggregates in brain, it is possible to assess the disease condition of the subject. Therefore, it is possible to plan for prevention/treatment of the disease (such as the type, combination, dosage, usage, and the like of a preventive/therapeutic agent to be administered) on the basis of the disease condition.

An embodiment of the present invention also relates to a medicament for treating or preventing a disease associated with α-synuclein aggregates, the medicament being administered in a dosage regimen based on data pertaining to the amount and/or distribution of α-synuclein aggregates in brain which is obtained by companion diagnosis.

[Diagnostic Kit for Diseases Associated with Substance Accumulated in Brain]

A diagnostic kit, in accordance with an embodiment of the present invention, for a disease associated with a substance accumulated in brain (hereinafter also referred to as "diagnostic kit") contains the above-described binding agent in accordance with the present embodiment.

The substance accumulated in the brain includes at least α-synuclein aggregates. The substance further includes aggregates of tau proteins and aggregates of amyloid-β peptides.

The disease associated with a substance accumulated in the brain includes at least diseases associated with α-synuclein aggregates. The diseases include Parkinson's disease, dementia with Lewy bodies (DLB), and multiple system atrophy (MSA). The disease associated with a substance accumulated in the brain also include Alzheimer's disease (AD) and frontotemporal lobar degeneration, each of which is a disease associated with aggregates of a tau protein or an amyloid-β peptide.

The binding agent in accordance with the present embodiment has higher binding selectivity with respect to α-synuclein aggregates than with respect to aggregates of a tau protein and aggregates of an amyloid-β peptide. In contrast, the inventors of the present invention found that the compound disclosed in Patent Literature 1, for example, has higher binding performance with respect to aggregates of a tau protein than with respect to α-synuclein aggregates.

In an aspect of the present embodiment, the diagnostic kit can contain both (i) the compound (I) or the compound (II), a pharmaceutically acceptable salt thereof, or a solvate thereof, each of which has high binding selectivity with respect to α-synuclein aggregates, and (ii) another compound which has high binding selectivity with respect to tau protein aggregates (e.g. the compound disclosed in Patent Literature 1). Such a diagnostic kit makes it possible to, by comparing a result of detection of the former (the amount and/or distribution of detected light or radioactivity) with a result of detection of the latter, determine which substance is present in each imaged area. Specifically, it is possible to classify α-synuclein aggregates and tau protein aggregates, and further possible to quantify the abundance of α-synuclein aggregates and tau protein aggregates. Thus, it is possible to diagnose, with high accuracy, a disease associated with α-synuclein aggregates and/or a disease associated with tau protein aggregates. For example, a ratio between binding performance with respect to α-synuclein aggregates and binding performance with respect to tau protein aggregates is previously determined for each of the binding agent in accordance with the present embodiment and a compound which has high binding selectivity with respect to tau protein aggregates (e.g., the compound disclosed in Patent Literature 1). By then measuring, in each area in the brain of a subject, a ratio between the amount of light or radioactivity after administration of the former and the amount of light or radioactivity after administration of the latter, it is possible to distinguish α-synuclein aggregates from tau protein aggregates in each area in the brain and quantify the abundance of those substances, based on a relation between the previously determined ratio and the measured ratio.

It is also possible to combine the diagnostic kit in accordance with the present embodiment with an imaging agent for an amyloid-β peptide. A diagnostic kit which is obtained by combining the diagnostic kit in accordance with the present embodiment with an imaging agent for an amyloid-β peptide makes it possible to determine substances present in each imaged area. Specifically, it is possible to distinguish between α-synuclein aggregates, tau protein aggregates, and amyloid-β aggregates, and further possible to quantify the abundance of the α-synuclein aggregates, the tau protein aggregates, and the amyloid-β aggregates. Thus, it is possible to diagnose, with high accuracy, a disease associated with α-synuclein aggregates, a disease associated with tau protein aggregates, and/or a disease associated with amyloid-β peptides.

An embodiment of the present invention also relates to a medicament for treating or preventing a disease associated with α-synuclein aggregates, the medicament being administered in a dosage regimen based on data pertaining to the amount and/or distribution of a substance, including α-synuclein aggregates and accumulated in the brain, which is obtained by the diagnostic kit in accordance with the present embodiment.

[Optical Imaging Method]

In an embodiment, the present invention provides a method for carrying out optical imaging. The method for carrying out optical imaging in accordance with the present embodiment (hereinafter also referred to as "optical imaging method") includes a step of detecting light which has a second wavelength and which is emitted from the brain of a living subject, after externally irradiating the brain with light which has a first wavelength, wherein the above-described binding agent in accordance with the present embodiment has been administered to the living subject, and the first wavelength and the second wavelength are different from each other.

In a case where an effective amount of the binding agent is administered to a subject, the binding agent that has been delivered to the brain of the subject binds to α-synuclein aggregates present in the brain. By externally irradiating the brain of the subject to which the binding agent has been administered with light which has the first wavelength and excites the binding agent, followed by detecting light (e.g., fluorescence) which is emitted from the binding agent in the brain and has the second wavelength, it is possible to carry out optical imaging of the α-synuclein aggregates.

The subject include mammals. Examples of the mammals include humans, rats, mice, rabbits, guinea pigs, hamsters, monkeys, dogs, ferrets, and minipigs.

An administration method is not particularly limited, and examples of the administration method include oral administration and parenteral administration such as intravenous administration and intraperitoneal administration. Preferably, intravenous or intraperitoneal administration is employed. Most preferably, intravenous administration is employed. A dose is preferably 0.01 mg/kg to 5 mg/kg, 0.05 mg/kg to 3 mg/kg, or 0.1 mg/kg to 1 mg/kg, and most preferably 0.1 mg/kg to 1 mg/kg.

[Radiological Imaging Method]

In an embodiment, the present invention provides a method for carrying out radiological imaging. The method for carrying out radiological imaging in accordance with the present embodiment (hereinafter also referred to as "radiological imaging method") includes a step of detecting radioactivity emitted from the brain of a living subject to which the binding agent in accordance with the present embodiment, which contains the compound (I) or the compound (II), in each of which at least one atom is a radioisotope thereof, a pharmaceutically acceptable salt thereof, or a solvate thereof, has been administered.

In a case where an effective amount of the binding agent is administered to a living subject, the binding agent that has been delivered to the brain of the living subject binds to α-synuclein aggregates present in the brain. By detecting radioactivity emitted from the binding agent in the brain, it is possible to carry out radiological imaging of the α-synuclein aggregates.

The subject include mammals. Examples of the mammals include humans, rats, mice, rabbits, guinea pigs, hamsters, monkeys, dogs, ferrets, and minipigs. Preferably, the mammals are humans.

An administration method is not particularly limited, and examples of the administration method include oral administration and parenteral administration such as intravenous administration and intraperitoneal administration. Preferably, intravenous or intraperitoneal administration is employed. Most preferably, intravenous administration is employed. A dose is preferably 5 ng/kg to 5 mg/kg, and more preferably 5 ng to 20 μg/kg. An applied radiation dose is preferably 37 MBq to 7.4 GBq, and more preferably 370 MBq to 3700 MBq, per individual.

[Method for Screening Therapeutic or Preventive Agent for Disease Associated with α-Synuclein Aggregates in Brain]

In an embodiment, the present invention provides a method for screening a therapeutic or preventive agent for a disease associated with α-synuclein aggregates in brain. The method for screening a therapeutic or preventive agent for a disease associated with α-synuclein aggregates in brain in accordance with the present embodiment (hereinafter also referred to as "screening method") includes a step of selecting a candidate agent on the basis of a difference, in amount and/or distribution of light or radioactivity which is detected by the optical imaging method or the radiological imaging method in accordance with the present embodiment, between before and after administration of the candidate agent to a subject.

The disease associated with α-synuclein aggregates in brain is similar to those described in the foregoing [Diagnostic kit for disease associated with substance accumulated in brain].

The subject and an administration method are similar to those described in the foregoing [Optical imaging method] and [radiological imaging method].

For example, in a case where, after administration of a candidate agent, the amount (intensity) of light (such as fluorescence) or radioactivity from the binding agent is reduced as compared with that before the administration of the candidate agent, the candidate agent can be useful as a therapeutic agent for the disease or symptom.

Moreover, in comparison of the amount and/or distribution of light or radioactivity detected in a subject with those/that in another healthy mammal, when the amount and/or distribution in the subject after administration of a candidate agent becomes closer to those/that in the healthy mammal, the candidate agent can be useful as a therapeutic agent for the disease or a symptom.

For example, data pertaining to the amount (intensity) and/or distribution of light (such as fluorescence) or radioactivity from the binding agent in a subject before and after the administration of a candidate agent is compared with an increase in the amount and/or changes in distribution of the same before and after the onset of a disease associated with α-synuclein aggregates in brain which has been preliminarily observed in a mammal without administration of the candidate agent. In a case where an increase in the amount of the light or radioactivity which is observed after the onset of the disease is suppressed by administration of the candidate agent and/or in a case where, after administration of the candidate agent, the amount of the light or radioactivity is similar to that before administration and is close to that in a healthy mammal, the candidate agent can be useful as a preventive compound for the disease or symptom. Similarly, in a case where changes in distribution of the light or radioactivity observed after the onset of a disease is suppressed by administration of the candidate agent and/or in a case where, after administration of the candidate agent, the changes in distribution of the light or radioactivity are similar to those before administration and are close to those in a healthy mammal, the candidate agent can be useful as a preventive agent for the disease or a symptom.

[Method for Quantifying or Determining Accumulation of α-Synuclein Aggregates in Brain]

In an embodiment, the present invention provides a method for quantifying or determining accumulation of α-synuclein aggregates in brain. The method for quantifying or determining accumulation of α-synuclein aggregates in brain in accordance with the present embodiment includes a step of detecting light which has a second wavelength and which is emitted from the brain of a living subject, after externally irradiating the brain with light which has a first wavelength, wherein the above-described binding agent which contains the compound (I) or the compound (II), a pharmaceutically acceptable salt thereof, or a solvate thereof has been administered to the living subject, and the first wavelength and the second wavelength are different from each other. Based on the amount and/or distribution of the detected light, accumulation of α-synuclein aggregates in the brain is quantified or determined. This method is a method for quantifying or determining accumulation of α-synuclein aggregates in brain by optical imaging.

The subject and an administration method are similar to those described in the foregoing [Optical imaging method].

By determining a difference(s) between the amount and/or distribution of light detected in a subject and those/that in a healthy mammal, it is possible to quantify accumulation of α-synuclein aggregates in the brain and to determine the presence or absence of the accumulation of α-synuclein aggregates in the brain.

In another aspect of the method for quantifying or determining accumulation of α-synuclein aggregates in brain in accordance with the present embodiment, the method includes a step of detecting radioactivity emitted from the brain of a living subject to which the binding agent in accordance with the present embodiment, which contains the compound (I) or the compound (II), in each of which at least one atom is a radioisotope thereof, a pharmaceutically acceptable salt thereof, or a solvate thereof, has been administered. On the basis of the amount and/or distribution of the detected radioactivity, accumulation of α-synuclein aggregates in the brain is quantified or determined. This method is a method for quantifying or determining accumulation of α-synuclein aggregates in brain by radiological imaging.

The subject and an administration method are similar to those described in the foregoing [Radiological imaging method].

By determining a difference(s) between the amount and/or distribution of light or radioactivity detected in a subject and those/that in a healthy mammal, it is possible to quantify accumulation of α-synuclein aggregates in the brain and to determine the presence or absence of the accumulation of α-synuclein aggregates in the brain.

[Method for Classifying Substance(s) Accumulated in Brain and Determining Accumulation of Substance(s)]

In an embodiment, the present invention provides a method for classifying a substance(s) accumulated in brain and determining accumulation of the substance(s). The method for classifying a substance(s) accumulated in brain and determining accumulation of the substance(s) in accordance with an embodiment of the present invention includes: a first step of detecting light which has a second wavelength and which is emitted from the brain of a living subject, after externally irradiating the brain with light which has a first wavelength, wherein the above-described binding agent in accordance with the present embodiment, which contains the compound (I) or the compound (II), a pharmaceutically acceptable salt thereof, or a solvate thereof, has been administered to the living subject, and the first wavelength and the second wavelength are different from each other; and a second step of detecting light which has a fourth wavelength and which is emitted from the brain of the living subject, after externally irradiating the brain with light which has a third wavelength, wherein a compound that has high binding selectivity with respect to tau protein aggregates (e.g., the compound disclosed in Patent Literature 1) has been administered to the living subject at a time point differing from the administration in the first step, and the third wavelength and the fourth wavelength are different from each other. Based on the data pertaining to the amount and/or distribution of the light detected in each of the first step and the second step, a substance(s) accumulated in the brain is/are classified, and accumulation of the substance(s) is determined. This method is a method for, by optical imaging, classifying a substance (s) accumulated in brain and determining accumulation of the substance(s).

The subject and an administration method are similar to those described in the foregoing [Optical imaging method].

The method includes both the first step of detecting light which is emitted from the brain and which results from administration of the binding agent having high binding selectivity with respect to α-synuclein aggregates and the second step of detecting light which is emitted from the brain of the same subject and which results from administration of the substance having high binding selectivity with respect to tau protein aggregates. Therefore, by comparing a result of detection in the first step (the amount and/or distribution of the detected light) with a result of detection in the second step, it is possible to classify a substance(s) accumulated in the brain into either α-synuclein aggregates or tau protein aggregates, and to determine the accumulation thereof.

In another aspect of the method for classifying a substance(s) accumulated in the brain and determining accumulation of the substance(s) in accordance with the present embodiment includes: a first step of detecting radioactivity emitted from the brain of a living subject to which the binding agent in accordance with the present embodiment, which contains the compound (I) or the compound (II), in each of which at least one atom is a radioisotope thereof, a pharmaceutically acceptable salt thereof, or a solvate thereof, has been administered; and a second step of detecting radioactivity which is emitted from the brain of the subject to which a compound that has high binding selectivity with respect to tau protein aggregates (e.g., the compound disclosed in Patent Literature 1) has been administered at a time point differing from that in the first step. Based on the data pertaining to the amount and/or distribution of the radioactivity detected in the first step and data pertaining to the amount and/or distribution of the radioactivity detected in the second step, a substance(s) accumulated in the brain is/are classified, and accumulation of the substance(s) is determined. This method is a method for, by radiological imaging, classifying a substance(s) accumulated in the brain and determining accumulation of the substance(s).

The subject and an administration method are similar to those described in the foregoing [Radiological imaging method].

The method includes both the first step of detecting radioactivity which is emitted from the brain and which results from administration of the binding agent having high binding selectivity with respect to α-synuclein aggregates and the second step of detecting radioactivity which is emitted from the brain of the same subject and which results from administration of the substance having high binding selectivity with respect to tau protein aggregates. Therefore, by comparing a result of detection in the first step (the amount and/or distribution of the detected radioactivity) with a result of detection in the second step, it is possible to carry out classification as to whether a substance(s) accumulated in the brain is/are α-synuclein aggregates and/or tau protein aggregates, and possible to determine accumulation of the substance(s).

(Summary)

The embodiments of the present invention are summarized below.

An aspect of the present invention is a compound represented by the following formula (I) or (II), a pharmaceutically acceptable salt thereof, or a solvate thereof.

(I)

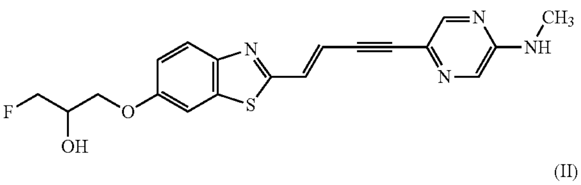

(II)

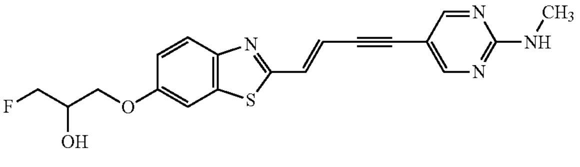

An aspect of the present invention is an α-synuclein aggregate binding agent containing the compound, the pharmaceutically acceptable salt, or the solvate.

An aspect of the present invention is a composition for optical imaging of α-synuclein aggregates, the composition containing the binding agent.

An aspect of the present invention is a composition for radiological imaging of α-synuclein aggregates, the composition containing the binding agent.

An aspect of the present invention is a method for carrying out optical imaging of α-synuclein aggregates in brain, the method including a step of detecting light which has a second wavelength and which is emitted from the brain of a living subject, after externally irradiating the brain with light which has a first wavelength, wherein the binding agent has been administered to the living subject, and the first wavelength and the second wavelength are different from each other.

An aspect of the present invention is a method for carrying out radiological imaging of α-synuclein aggregates in brain, the method including the step of detecting radioactivity which is emitted from the brain of a living subject to which the binding agent has been administered.

An aspect of the present invention is an intermediate for synthesizing the compound, the intermediate being represented by the following formula (III):

(III)

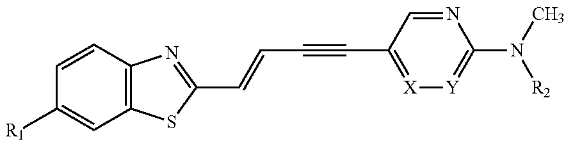

wherein:

one of X and Y is a nitrogen atom (N), and the other is an unsubstituted carbon atom (CH) (i.e., in a case where X is a nitrogen atom, Y is an unsubstituted carbon atom (CH), whereas in a case where X is an unsubstituted carbon atom (CH), Y is a nitrogen atom);

$R_1$ is a hydroxy group or a group represented by the following formula (i):

(i)

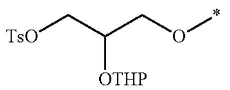

wherein Ts represents a p-toluenesulfonyl group, THP represents a tetrahydro-2H-pyran-2-yl group, and

* represents a position to which a benzothiazole ring binds; and $R_2$ is a hydrogen atom or a tert-butoxycarbonyl (Boc) group.

An aspect of the present invention is a diagnostic kit including the compound (I) or the compound (II) each of which has high binding selectivity with respect to α-synuclein aggregates.

The present invention is not limited to the embodiments, but can be altered by a skilled person in the art within the scope of the claims. The present invention also encompasses, in its technical scope, any embodiment derived by combining technical means disclosed in differing embodiments.

EXAMPLES

Production Examples

In production examples (Reference Examples and Examples) below, the "room temperature" generally indicates a temperature of approximately 10° C. to approximately 35° C. The "%" indicates "% by weight", unless otherwise specified. In description of a compound used in each production example, the expression "produced in Reference Example (Example) X" is intended to also include a case of "produced in a manner similar to that in Reference Example (Example) X".

Elution in column chromatography in each production example was carried out under observation by thin layer chromatography (TLC), unless otherwise specified. In the TLC observation, 60 F254, manufactured by Merck, was used as a TLC plate, and a solvent used as an elution solvent in the column chromatography was used as a developing solvent. For detection, a UV detector was employed.

ACD/SpecManager (product name) software and the like were used to analyze $^1$H NMR, and values obtained by the analysis were shown. A proton peak which was extremely gentle, such as those of a hydroxy group and an amino group, may not be shown.

In Examples below, the following abbreviations are used.

M: molar concentration

DMSO-$d_6$: deuterated dimethyl sulfoxide $^1$H NMR: proton nuclear magnetic resonance DIEA: N-ethyl-N-isopropylpropan-2-amine DMF: N,N-dimethylformamide (herein, also referred to as "dimethylformamide")

THF: tetrahydrofuran

MeOH: methanol

EtOH: ethanol

DMSO: dimethyl sulfoxide

TEA: triethylamine

TFA: trifluoroacetic acid

Reference Example 1: Production of di-tert-butyl (5-iodopyrazin-2-yl)-2-imidodicarbonate

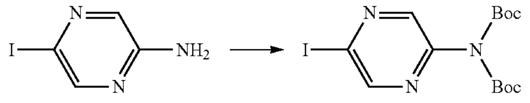

To a solution of 5-iodopyrazin-2-amine (CAS [886860-50-0]) (10.5 g) in THF (100 ml) were added a solution of di-tert-butyl dicarbonate (25.9 g) in THF (50 ml) and N,N-dimethylpyridin-4-amine (1.45 g) at 0° C. The mixture was stirred at 0° C. to room temperature overnight, and diluted with water and ethyl acetate. The insoluble was removed by filtration and the filtrate was extracted with ethyl acetate. The extract was washed with water and brine, dried over anhydrous sodium sulfate, passed through a short silica gel column, and concentrated under reduced pressure to obtain the title compound (18.8 g) as a brown solid. $^1$H NMR (300 MHz, DMSO-$d_6$) δ 1.37-1.41 (18H, m), 8.65 (1H, d, J=1.3 Hz), 8.90 (1H, d, J=1.5 Hz)

Reference Example 2: Production of tert-butyl (5-iodopyrazin-2-yl)carbamate

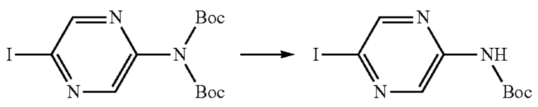

To a solution of di-tert-butyl (5-iodopyrazin-2-yl)-2-imidodicarbonate (18.8 g) produced in Reference Example 1 in MeOH (200 ml), was added potassium carbonate (7.40 g) at room temperature. The mixture was stirred at room temperature for 2 h, concentrated to approximately a quarter volume under reduced pressure, cooled to 0° C., neutralized with 5% citric acid solution, and diluted with water. The precipitated solid was collected by filtration, washed with water, and dried to obtain the title compound (13.7 g) as a brown solid.

$^1$H NMR (300 MHz, DMSO-$d_6$) δ 1.47 (9H, s), 8.55 (1H, d, J=1.3 Hz), 8.87 (1H, d, J=1.5 Hz), 10.29 (1H, brs)

Reference Example 3: Production of tert-butyl (5-iodopyrazin-2-yl)(methyl)carbamate

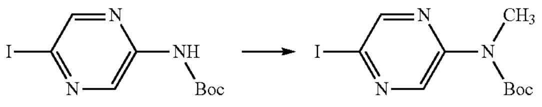 [SMILES: CC(C)(C)OC(=O)Nc1cnc(I)cn1 ; CN(C(=O)OC(C)(C)C)c1cnc(I)cn1]

To a solution of tert-butyl (5-iodopyrazin-2-yl)carbamate (13.7 g) produced in Reference Example 2 and cesium carbonate (20.9 g) in DMF (85 ml), was added methyl iodide (3.45 ml) at 0° C. The mixture was stirred at 0° C. to room temperature overnight, cooled to 0° C., and diluted with water. The precipitated solid was collected by filtration, washed with water, and dried to obtain the title compound (13.0 g) as a beige solid. $^1$H NMR (300 MHz, DMSO-$d_6$) δ 1.49 (9H, s), 3.27 (3H, s), 8.72 (1H, d, J=1.5 Hz), 8.83 (1H, d, J=1.5 Hz)

Reference Example 4: Production of tert-butyl (5-(3-hydroxyprop-1-yn-1-yl) pyrazin-2-yl)(methyl) carbamate

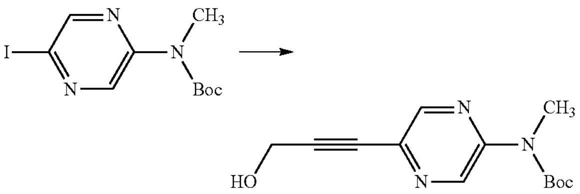

To a solution of tert-butyl (5-iodopyrazin-2-yl)(methyl) carbamate (13.0 g) produced in Reference Example 3, 2-propyn-1-ol (3.43 ml), and copper iodide (I) (739 mg) in TEA (27 ml) and THF (27 ml), was added dichlorobis (triphenylphosphine)palladium (II) (545 mg) at room temperature under nitrogen atmosphere. The mixture was stirred at room temperature for 2 h, diluted with ethyl acetate, and filtered through a celite pad. The filtrate was concentrated under reduced pressure. The residue was diluted with ethyl acetate, acidified with 5% citric acid solution, filtered through a celite pad, and extracted with ethyl acetate. The extract was washed with water and brine, dried over anhydrous sodium sulfate, passed through a silica gel pad, and concentrated under reduced pressure to obtain the title compound (10.2 g) as a brown solid. $^1$H NMR (300 MHz, DMSO-$d_6$) δ 1.50 (9H, s), 3.31 (3H, s), 4.35 (2H, d, J=6.0 Hz), 5.48 (1H, t, J=6.0 Hz), 8.52 (1H, d, J=1.5 Hz), 8.98 (1H, d, J=1.5 Hz)

Reference Example 5: Production of tert-butyl (5-(3-hydroxyprop-1-yn-1-yl)pyrimidin-2-yl)(methyl) carbamate

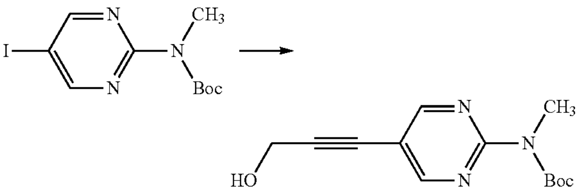

The title compound (195 mg) was obtained as a brown solid, in a manner similar to that in Reference Example 4 with use of tert-butyl (5-iodopyrimidin-2-yl)(methyl)carbamate (CAS [1578264-18-2]) (250 mg). $^1$H NMR (300 MHz, DMSO-$d_6$) δ 1.44 (9H, s), 3.31 (3H, s), 4.34 (2H, d, J=5.7 Hz), 5.44 (1H, t, J=5.8 Hz), 8.77 (2H, s)

Reference Example 6: Production of tert-butyl methyl(5-(3-oxoprop-1-yn-1-yl) pyrazin-2-yl)carbamate

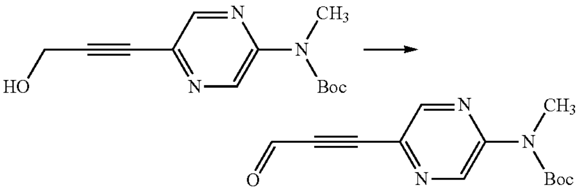

To a solution of tert-butyl(5-(3-hydroxyprop-1-yn-1-yl) pyrazin-2-yl)(methyl)carbamate (10.4 g) produced in Reference Example 4 in acetonitrile (200 ml) was added 1,1,1-triacetoxy-1,1-dihydro-1,2-benziodoxol-3-(1H)-one (20.1 g) at room temperature. The mixture was stirred at room temperature for 2 h and cooled to 0° C. To the mixture were added saturated sodium thiosulfate solution and 5% sodium bicarbonate solution. The mixture was stirred for 5 min and extracted with ethyl acetate. The extract was washed with water and brine, dried over anhydrous sodium sulfate, passed through a short silica gel column, and concentrated under reduced pressure. The residue was purified by silica gel column chromatography (hexane/ethyl acetate) to obtain the title compound (6.20 g) as a yellow solid. $^1$H NMR (300 MHz, DMSO-$d_6$) δ 1.52 (9H, s), 3.35 (3H, s), 8.82 (1H, d, J=1.3 Hz), 9.17 (1H, d, J=1.5 Hz), 9.48 (1H, s)

Reference Example 7: Production of tert-butyl methyl(5-(3-oxoprop-1-yn-1-yl)pyrimidin-2-yl)carbamate

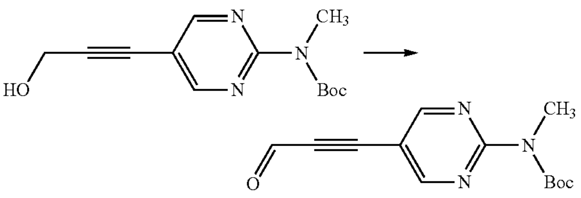

The title compound (149 mg) was obtained as a white solid, in a manner similar to that in Reference Example 6 with use of tert-butyl (5-(3-hydroxyprop-1-yn-1-yl)pyrimidin-2-yl)(methyl)carbamate (190 mg) produced in Reference Example 5.

$^1$H NMR (300 MHz, DMSO-$d_6$) δ 1.47 (9H, s), 3.36 (3H, s), 9.00 (2H, s), 9.46 (1H, s)

Reference Example 8: Production of 2-((1-(benzyloxy)-3-fluoropropan-2-yl)oxy)tetrahydro-2H-pyrane

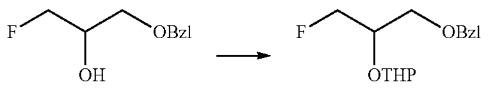

To a solution of 1-(benzyloxy)-3-fluoropropan-2-ol (CAS [112482-36-7]) (6.37 g) and 3,4-dihydro-2H-pyrane (3.75 ml) in THF (67 ml), was added p-toluenesulfonic acid monohydrate (132 mg) at room temperature. The mixture was stirred at room temperature overnight. DIEA (0.242 ml) was added to the mixture. The mixture was concentrated under reduced pressure. The residue was purified by silica gel column chromatography (hexane/ethyl acetate) to obtain the title compound (8.37 g) as a colorless oil. $^1$H NMR (300 MHz, DMSO-$d_6$) δ 1.35-1.54 (4H, m), 1.56-1.80 (2H, m), 3.36-3.47 (1H, m), 3.48-3.63 (2H, m), 3.80 (1H, ddd, J=11.2, 7.9, 3.4 Hz), 3.90-4.06 (1H, m), 4.35-4.70 (2H, m), 4.51 (2H, d, J=2.1 Hz), 4.74-4.81 (1H, m), 7.24-7.41 (5H, m)

Reference Example 9: Production of 2-(((R)-1-(benzyloxy)-3-fluoropropan-2-yl)oxy)tetrahydro-2H-pyrane

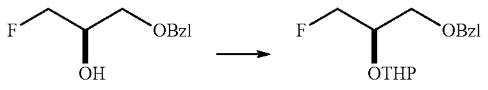

The title compound (10.36 g) was obtained as a colorless oil, in a manner similar to that in Reference Example 8 with use of (R)-1-(benzyloxy)-3-fluoropropan-2-ol (CAS [147332-34-1]) (7.85 g).

$^1$H NMR (300 MHz, DMSO-$d_6$) δ 1.47 (4H, br dd, J=7.4, 3.9 Hz), 1.56-1.80 (2H, m), 3.35-3.47 (1H, m), 3.47-3.63 (2H, m), 3.80 (1H, ddd, J=11.3, 8.0, 3.4 Hz), 3.89-4.11 (1H, m), 4.34-4.69 (4H, m), 4.73-4.83 (1H, m), 7.19-7.49 (5H, m)

Reference Example 10: Production of 2-(((S)-1-(benzyloxy)-3-fluoropropan-2-yl)oxy)tetrahydro-2H-pyrane

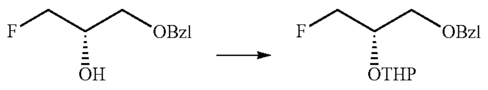

The title compound (10.48 g) was obtained as a colorless oil, in a manner similar to that in Reference Example 8 with use of (S)-1-(benzyloxy)-3-fluoropropan-2-ol (CAS [1707146-21-1]) (7.55 g).

$^1$H NMR (300 MHz, DMSO-$d_6$) δ 1.47 (4H, br dd, J=7.4, 3.9 Hz), 1.56-1.79 (2H, m), 3.35-3.47 (1H, m), 3.48-3.62 (2H, m), 3.80 (1H, ddd, J=11.2, 7.9, 3.3 Hz), 3.90-4.08 (1H, m), 4.35-4.70 (4H, m), 4.73-4.81 (1H, m), 7.24-7.42 (5H, m)

Reference Example 11: Production of 3-(benzyloxy)-2-((tert-butyldimethylsilyl)oxy)propyl 4-methylbenzenesulfonate

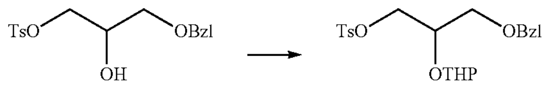

To a solution of 3-(benzyloxy)-2-hydroxypropyl 4-methylbenzenesulfonate (CAS [99881-48-8]) (2.80 g) and 1H-imidazole (737 mg) in DMF (30 ml), was added tert-butyldimethylchlorosilane (1.51 g) at 0° C. The mixture was stirred at room temperature overnight, cooled to 0° C., diluted with water and ethyl acetate, acidified to pH approximately 5 with 5% citric acid solution, and extracted with ethyl acetate. The extract was washed with water and brine, dried over anhydrous sodium sulfate, and concentrated under reduced pressure. The residue was purified by silica gel column chromatography (hexane/ethyl acetate) to obtain the title compound (3.37 g) as a colorless oil.

$^1$H NMR (300 MHz, DMSO-$d_6$) δ −0.02 (6H, d, J=1.1 Hz), 0.79 (9H, s), 2.41 (3H, s), 3.36 (2H, d, J=5.3 Hz), 3.86-4.05 (3H, m), 4.43 (2H, s), 7.20-7.39 (5H, m), 7.47 (2H, d, J=8.1 Hz), 7.77 (2H, d, J=8.3 Hz)

Reference Example 12: Production of 3-fluoro-2-((tetrahydro-2H-pyran-2-yl)oxy)propan-1-ol

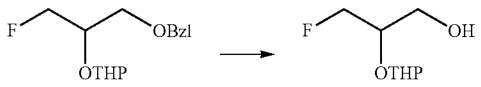

A mixture of 2-((1-(benzyloxy)-3-fluoropropan-2-yl)oxy)tetrahydro-2H-pyrane (8.30 g) produced in Reference Example 8, 10% palladium-carbon (containing 50% water, 1.98 g) and EtOH (85 ml) was stirred at room temperature overnight under hydrogen atmosphere at ambient pressure. The catalyst was removed by filtration. The filtrate was concentrated under reduced pressure to obtain the title compound (5.45 g) as a colorless oil.

$^1$H NMR (300 MHz, DMSO-$d_6$) δ 1.33-1.55 (4H, m), 1.56-1.86 (2H, m), 3.36-3.58 (3H, m), 3.68-3.88 (2H, m), 4.31-4.70 (2H, m), 4.71-4.86 (2H, m)

Reference Example 13: Production of (2R)-3-fluoro-2-((tetrahydro-2H-pyran-2-yl)oxy)propan-1-ol

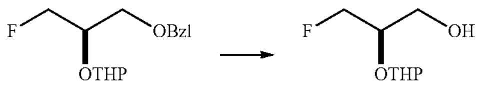

The title compound (6.85 g) was obtained as a colorless oil, in a manner similar to that in Reference Example 12 with use of 2-(((R)-1-(benzyloxy)-3-fluoropropan-2-yl)oxy)tetrahydro-2H-pyrane (10.35 g) produced in Reference Example 9.

$^1$H NMR (300 MHz, DMSO-$d_6$) δ 1.35-1.53 (4H, m), 1.55-1.81 (2H, m), 3.37-3.62 (3H, m), 3.67-3.91 (2H, m), 4.29-4.69 (2H, m), 4.71-4.87 (2H, m)

Reference Example 14: Production of (2S)-3-fluoro-2-((tetrahydro-2H-pyran-2-yl)oxy)propan-1-ol

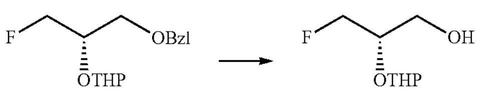

The title compound (6.90 g) was obtained as a colorless oil, in a manner similar to that in Reference Example 12 with use of 2-(((S)-1-(benzyloxy)-3-fluoropropan-2-yl)oxy)tetrahydro-2H-pyrane (10.45 g) produced in Reference Example 10.

$^1$H NMR (300 MHz, DMSO-$d_6$) δ 1.33-1.56 (4H, m), 1.57-1.81 (2H, m), 3.35-3.59 (3H, m), 3.69-3.90 (2H, m), 4.31-4.68 (2H, m), 4.71-4.87 (2H, m)

Reference Example 15: Production of 2-((tert-butyldimethylsilyl)oxy)-3-hydroxypropyl 4-methylbenzenesulfonate

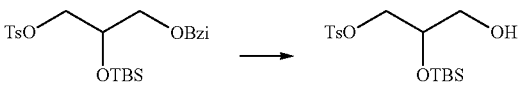

The title compound (2.66 g) was obtained as a colorless oil, in a manner similar to that in Reference Example 12 with use of 3-(benzyloxy)-2-((tert-butyldimethylsilyl)oxy)propyl 4-methylbenzenesulfonate (3.36 g) produced in Reference Example 11.

$^1$H NMR (300 MHz, DMSO-$d_6$) δ −0.01 (3H, s), 0.01 (3H, s), 0.80 (9H, s), 2.42 (3H, s), 3.20-3.38 (2H, m), 3.75-3.91 (2H, m), 4.02-4.10 (1H, m), 4.81 (1H, t, J=5.6 Hz), 7.49 (2H, dd, J=8.6, 0.7 Hz), 7.77 (2H, d, J=8.3 Hz)

Reference Example 16: Production of mixture of (2S)-3-fluoro-2-((tetrahydro-2H-pyran-2-yl)oxy)propan-1-ol and (2S)-1-fluoro-3-((tetrahydro-2H-pyran-2-yl)oxy)propan-2-ol

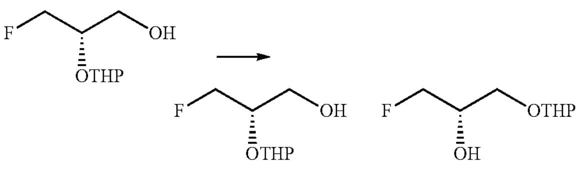

The title mixture of compounds (6.90 g) was obtained as a colorless oil by storing (2S)-3-fluoro-2-((tetrahydro-2H-pyran-2-yl)oxy)propan-1-ol (6.90 g) produced in Reference Example 14 at room temperature.

$^1$H NMR (300 MHz, DMSO-$d_6$) δ 1.33-1.54 (4H, m), 1.56-1.85 (2H, m), 3.28-3.96 (5H, m), 4.18-4.92 (3H, m), 4.92-5.20 (1H, m)

Reference Example 17: Production of diethyl ((6-((tert-butyldimethylsilyl)oxy)benzo[d]thiazol-2-yl)methyl)phosphonate

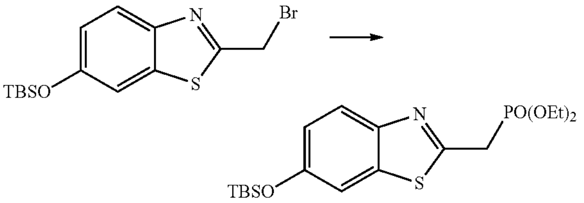

A mixture of 2-(bromomethyl)-6-((tert-butyldimethylsilyl)oxy)benzo[d]thiazole (CAS [1638685-65-0]) (3.06 g) and triethyl phosphite (1.78 ml) was stirred at 100° C. for 3 h, cooled to room temperature, and purified by silica gel column chromatography (ethyl acetate/methanol) to obtain the title compound (2.39 g) as a yellow oil.

$^1$H NMR (300 MHz, DMSO-$d_6$) δ 0.22 (6H, s), 0.97 (9H, s), 1.23 (6H, t, J=7.0 Hz), 3.80-3.92 (2H, m), 4.01-4.13 (4H, m), 7.00 (1H, dd, J=8.7, 2.5 Hz), 7.56 (1H, d, J=2.4 Hz), 7.81 (1H, d, J=8.8 Hz)

Reference Example 18: Production of diethyl ((6-hydroxybenzo[d]thiazol-2-yl)methyl)phosphonate

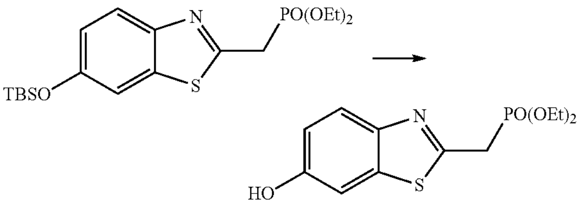

To a solution of diethyl ((6-((tert-butyldimethylsilyl)oxy)benzo[d]thiazol-2-yl)methyl)phosphonate (4.87 g) produced in Reference Example 17 in THF (50 ml), was added tetra-n-butylammonium fluoride (1M THF solution, 12.9 ml) at room temperature. The mixture was stirred at room temperature for 1 h, diluted with water, and extracted with ethyl acetate. The extract was washed with water and brine, dried over anhydrous sodium sulfate, and concentrated under reduced pressure. The residual solid was suspended in hexane/ethyl acetate, collected by filtration, washed with hexane/ethyl acetate, and dried to obtain the title compound (2.85 g) as a yellow solid.

$^1$H NMR (300 MHz, DMSO-$d_6$) δ 1.22 (6H, t, J=7.1 Hz), 3.81 (2H, d, J=21.4 Hz), 4.05 (4H, dq, J=8.3, 7.1 Hz), 6.93 (1H, dd, J=8.8, 2.5 Hz), 7.34 (1H, d, J=2.4 Hz), 7.73 (1H, d, J=8.8 Hz), 9.78 (1H, brs)

Reference Example 19: Production of diethyl ((6-(3-fluoro-2-((tetrahydro-2H-pyran-2-yl)oxy)propoxy)benzo[d]thiazol-2-yl)methyl)phosphonate

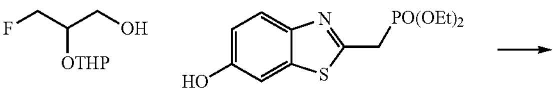

-continued

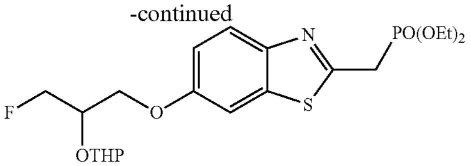

To a solution of diethyl ((6-hydroxybenzo[d]thiazol-2-yl) methyl)phosphonate (2.84 g) produced in Reference Example 18, 3-fluoro-2-((tetrahydro-2H-pyran-2-yl)oxy) propan-1-ol (2.52 g) produced in Reference Example 12, and triphenylphosphine (4.20 g) in THF (50 ml), was added diisopropyl azodicarboxylate (3.15 ml) at room temperature. The mixture was stirred at room temperature for 1 day. Then, 3-fluoro-2-((tetrahydro-2H-pyran-2-yl)oxy)propan-1-ol (0.504 g) produced in Reference Example 12, triphenylphosphine (0.742 g), and diisopropyl azodicarboxylate (0.555 ml) were added to the mixture at room temperature. The mixture was stirred at room temperature overnight, and concentrated under reduced pressure. The residue was purified by silica gel column chromatography (hexane/ethyl acetate) to obtain the title compound (3.78 g) as a yellow oil.

$^1$H NMR (300 MHz, DMSO-$d_6$) δ 1.22 (6H, t, J=7.0 Hz), 1.37-1.56 (4H, m), 1.59-1.80 (2H, m), 3.41-3.53 (1H, m), 3.78-3.94 (3H, m), 4.01-4.11 (4H, m), 4.12-4.29 (3H, m), 4.48-4.65 (1H, m), 4.65-4.81 (1H, m), 4.83-4.94 (1H, m), 7.12 (1H, dt, J=9.0, 2.1 Hz), 7.70 (1H, d, J=2.4 Hz), 7.84 (1H, d, J=8.9 Hz)

Reference Example 20: Production of tert-butyl (E)-(5-(4-(6-(3-fluoro-2-((tetrahydro-2H-pyran-2-yl) oxy)propoxy)benzo[d]thiazol-2-yl)but-3-en-1-yn-1-yl)pyrazin-2-yl)(methyl)carbamate

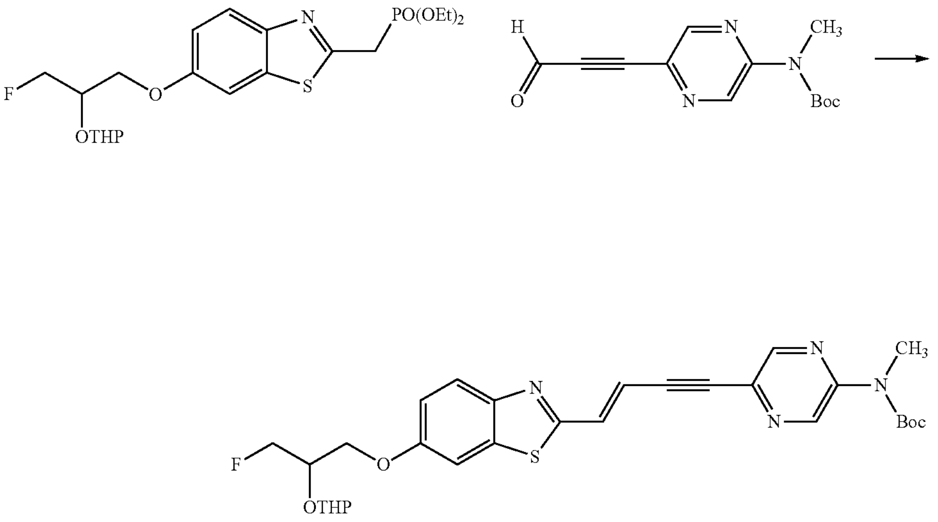

To a solution of diethyl ((6-(3-fluoro-2-((tetrahydro-2H-pyran-2-yl)oxy)propoxy)benzo[d]thiazol-2-yl)methyl)phosphonate (3.77 g) produced in Reference Example 19 and tert-butyl methyl(5-(3-oxoprop-1-yn-1-yl)pyrazin-2-yl)carbamate (2.56 g) produced in Reference Example 6 in THF (30 ml), was added sodium hydride (60% in oil, 392 mg) at 0° C. The mixture was stirred at 0° C. for 10 min. DMF (30 ml) was added to the mixture at 0° C. The mixture was stirred at 0° C. to room temperature for 3 h. Tert-butyl methyl(5-(3-oxoprop-1-yn-1-yl)pyrazin-2-yl)carbamate (256 mg) produced in Reference Example 6 was added to the mixture at room temperature. The mixture was stirred at room temperature for 1 h, diluted with ethyl acetate and water, neutralized with 5% citric acid solution, and extracted with ethyl acetate. The extract was washed with water and brine, dried over anhydrous sodium sulfate, and concentrated under reduced pressure. The residue was purified by silica gel column chromatography (hexane/ethyl acetate). The fractions containing the desired compound were concentrated under reduced pressure. The residual solid was suspended in hexane, collected by filtration, washed with hexane, and dried to obtain the title compound (2.06 g) as a yellow solid.

$^1$H NMR (300 MHz, DMSO-$d_6$) δ 1.39-1.58 (13H, m), 1.59-1.81 (2H, m), 3.33 (3H, s), 3.41-3.52 (1H, m), 3.78-3.95 (1H, m), 4.13-4.31 (3H, m), 4.48-4.66 (1H, m), 4.66-4.83 (1H, m), 4.84-4.93 (1H, m), 7.01 (1H, d, J=16.2 Hz), 7.17 (1H, dt, J=9.0, 2.2 Hz), 7.48 (1H, d, J=16.0 Hz), 7.77 (1H, d, J=2.4 Hz), 7.92 (1H, d, J=8.9 Hz), 8.65 (1H, d, J=1.5 Hz), 9.06 (1H, d, J=1.5 Hz)

Example 1: Production of tert-butyl (E)-(5-(4-(6-hydroxybenzo[d]thiazol-2-yl)but-3-en-1-yn-1-yl)pyrazin-2-yl)(methyl)carbamate

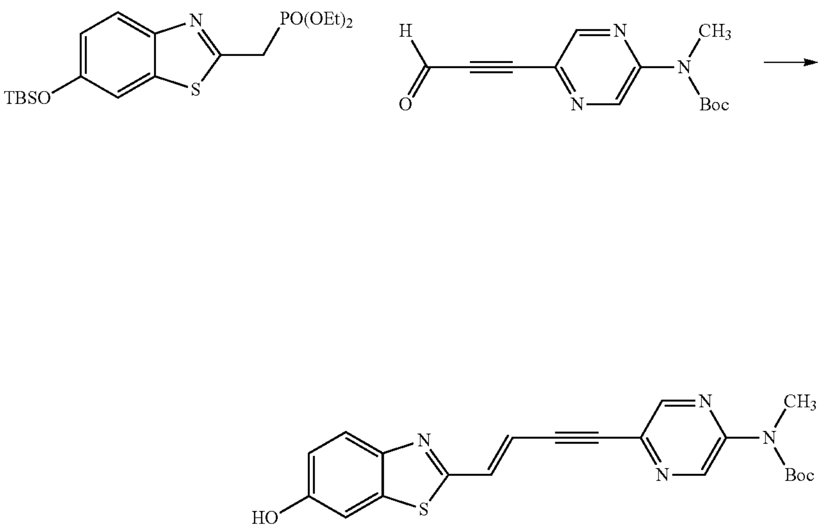

To a solution of diethyl ((6-((tert-butyldimethylsilyl)oxy)benzo[d]thiazol-2-yl)methyl)phosphonate (2.39 g) produced in Reference Example 17 and tert-butyl methyl(5-(3-oxoprop-1-yn-1-yl)pyrazin-2-yl)carbamate (1.65 g) produced in Reference Example 6 in THF (25 ml), was added sodium hydride (60% in oil, 322 mg) at 0° C. The mixture was stirred at 0° C. for 5 min. DMF (25 ml) was added to the mixture at 0° C. The mixture was stirred at 0° C. for 2 h. Sodium hydride (60% in oil, 138 mg) and tert-butyl methyl (5-(3-oxoprop-1-yn-1-yl)pyrazin-2-yl)carbamate (601 mg) produced in Reference Example 6 were added to the mixture at 0° C. The mixture was stirred at 0° C. to room temperature for 2 h, cooled to 0° C., acidified to pH approximately 5 with 5% citric acid solution, diluted with water, and extracted with ethyl acetate. The extract was washed with water and brine, dried over anhydrous sodium sulfate, passed through a short silica gel column, and concentrated under reduced pressure. The residual solid was suspended in ethyl acetate/hexane, collected by filtration, washed with ethyl acetate/hexane, and dried to obtain the title compound (1.85 g) as a yellow solid.

$^1$H NMR (300 MHz, DMSO-$d_6$) δ 1.51 (9H, s), 3.33 (3H, s), 6.94 (1H, d, J=16.0 Hz), 7.00 (1H, dd, J=8.9, 2.4 Hz), 7.39 (1H, d, J=2.3 Hz), 7.44 (1H, d, J=16.0 Hz), 7.82 (1H, d, J=8.9 Hz), 8.64 (1H, d, J=1.5 Hz), 9.05 (1H, d, J=1.5 Hz), 10.14 (1H, brs)

Example 2: Production of tert-butyl (E)-(5-(4-(6-hydroxybenzo[d]thiazol-2-yl)but-3-en-1-yn-1-yl)pyrimidin-2-yl)(methyl)carbamate

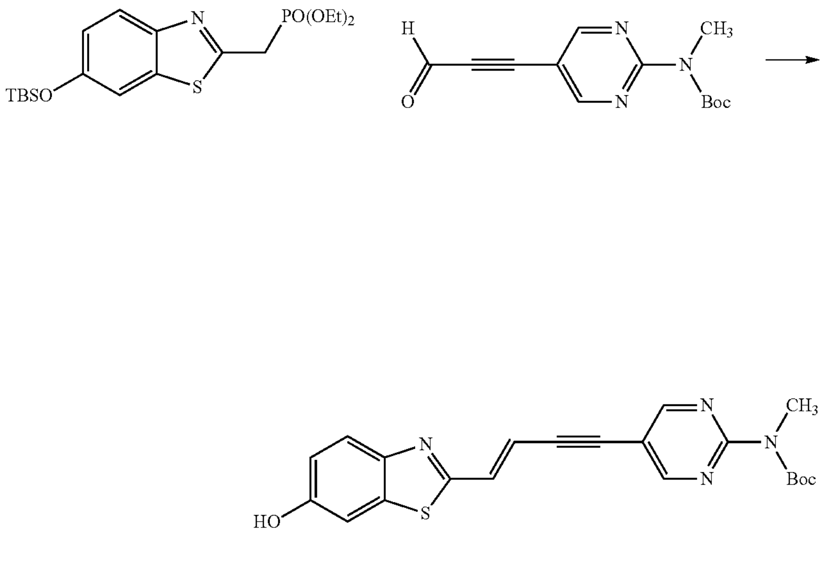

The title compound (101 mg) was obtained as a yellow solid, in a manner similar to that in Example 1 with use of diethyl ((6-((tert-butyldimethylsilyl)oxy)benzo[d]thiazol-2-yl)methyl)phosphonate (254 mg) produced in Reference Example 17 and tert-butyl methyl(5-(3-oxoprop-1-yn-1-yl) pyrimidin-2-yl)carbamate (145 mg) produced in Reference Example 7.

$^1$H NMR (300 MHz, DMSO-$d_6$) δ 1.46 (9H, s), 3.34 (3H, s), 6.92 (1H, d, J=16.0 Hz), 7.00 (1H, dd, J=8.9, 2.4 Hz), 7.38 (1H, d, J=16.0 Hz), 7.39 (1H, d, J=2.4 Hz), 7.82 (1H, d, J=8.9 Hz), 8.87 (2H, s), 10.01 (1H, s)

Reference Example 21: Production of tert-butyl (5-((E)-4-(6-((2R)-3-fluoro-2-((tetrahydro-2H-pyran-2-yl)oxy)propoxy)benzo[d]thiazol-2-yl)but-3-en-1-yn-1-yl) pyrazin-2-yl)(methyl) carbamate

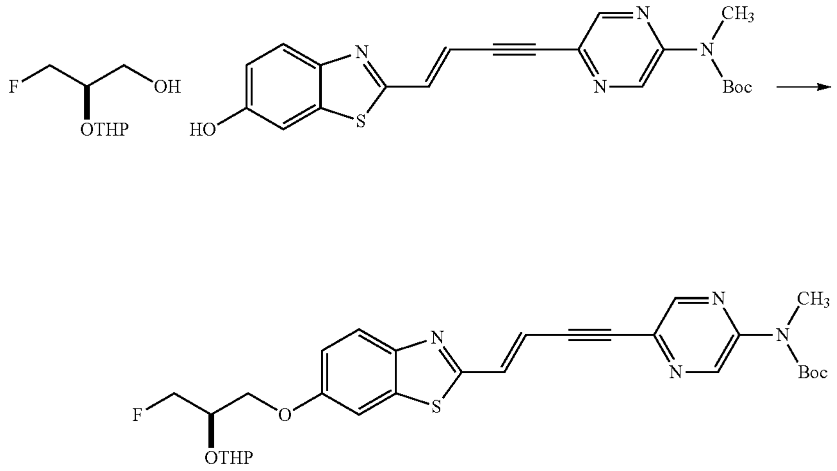

The title compound (100 mg) was obtained as a pale-yellow solid, in a manner similar to that in Reference Example 19 with use of tert-butyl (E)-(5-(4-(6-hydroxy-benzo[d]thiazol-2-yl)but-3-en-1-yn-1-yl)pyrazin-2-yl) (methyl)carbamate (100 mg) produced in Example 1, (2R)-3-fluoro-2-((tetrahydro-2H-pyran-2-yl)oxy)propan-1-ol (114 mg) produced in Reference Example 13, and bis(2-methoxyethyl) azodicarboxylate (172 mg).

$^1$H NMR (300 MHz, DMSO-$d_6$) δ 1.51 (13H, s), 1.60-1.79 (2H, m), 3.34 (3H, s), 3.42-3.54 (1H, m), 3.79-3.96 (1H, m), 4.14-4.31 (3H, m), 4.49-4.82 (2H, m), 4.84-4.96 (1H, m), 7.02 (1H, d, J=16.1 Hz), 7.17 (1H, dt, J=9.0, 2.1 Hz), 7.48 (1H, d, J=16.1 Hz), 7.77 (1H, d, J=2.5 Hz), 7.92 (1H, d, J=9.0 Hz), 8.65 (1H, d, J=1.4 Hz), 9.06 (1H, d, J=1.5 Hz)

Reference Example 22: Production of tert-butyl (5-((E)-4-(6-((2S)-3-fluoro-2-((tetrahydro-2H-pyran-2-yl)oxy)propoxy)benzo[d]thiazol-2-yl)but-3-en-1-yn-1-yl) pyrazin-2-yl)(methyl)carbamate

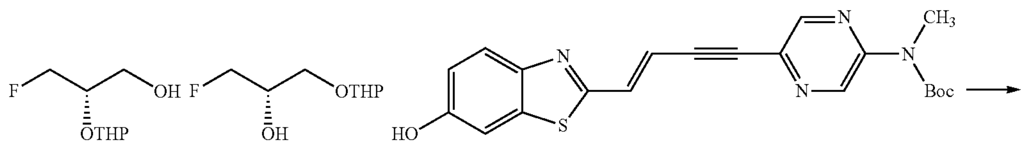

-continued

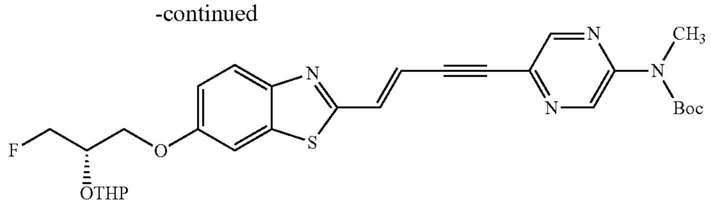

The title compound (22 mg) was obtained as a pale-yellow solid, in a manner similar to that in Reference Example 19 with use of tert-butyl (E)-(5-(4-(6-hydroxy-benzo[d]thiazol-2-yl)but-3-en-1-yn-1-yl)pyrazin-2-yl)(methyl)carbamate (100 mg) produced in Example 1, a mixture (114 mg) of (2S)-3-fluoro-2-((tetrahydro-2H-pyran-2-yl)oxy)propan-1-ol and (2S)-1-fluoro-3-((tetrahydro-2H-pyran-2-yl)oxy)propan-2-ol produced in Reference Example 16, and bis(2-methoxyethyl) azodicarboxylate (172 mg).

$^1$H NMR (300 MHz, DMSO-$d_6$) δ 1.51 (13H, s), 1.60-1.79 (2H, m), 3.34 (3H, s), 3.42-3.54 (1H, m), 3.79-3.95 (1H, m), 4.13-4.30 (3H, m), 4.49-4.82 (2H, m), 4.84-4.96 (1H, m), 7.02 (1H, d, J=16.2 Hz), 7.17 (1H, dd, J=8.8, 2.4 Hz), 7.48 (1H, d, J=16.0 Hz), 7.77 (1H, d, J=2.3 Hz), 7.92 (1H, d, J=9.0 Hz), 8.65 (1H, d, J=1.3 Hz), 9.06 (1H, d, J=1.3 Hz)

Reference Example 23: Production of (E)-3-((2-(4-(5-((tert-butoxycarbonyl)(methyl)amino)pyrazin-2-yl)but-1-en-3-yn-1-yl)benzo[d]thiazol-6-yl)oxy)-2-((tert-butyldimethylsilyl)oxy)propyl 4-methylbenzenesulfonate

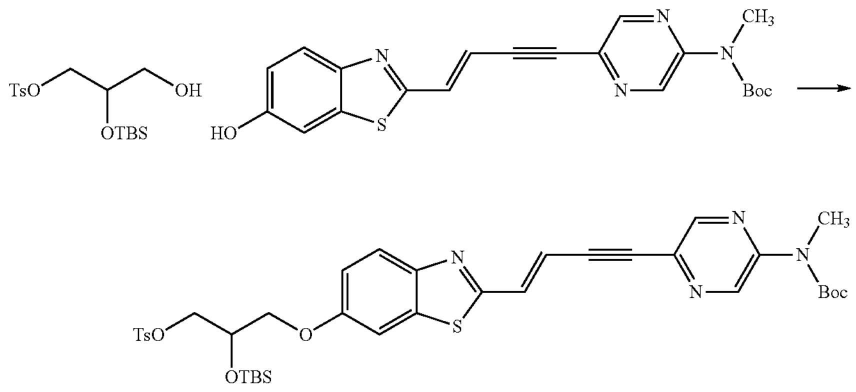 [SMILES: Cc1ccc(S(=O)(=O)OCC(CO)O[Si](C)(C)C(C)(C)C)cc1 ; CN(C(=O)OC(C)(C)C)c1cnc(C#C/C=C/c2nc3ccc(O)cc3s2)cn1 ; Cc1ccc(S(=O)(=O)OCC(COc2ccc3nc(/C=C/C#Cc4cnc(N(C)C(=O)OC(C)(C)C)cn4)sc3c2)O[Si](C)(C)C(C)(C)C)cc1]

The title compound (1.47 g) was obtained as a pale-yellow solid, in a manner similar to that in Reference Example 19 with use of tert-butyl (E)-(5-(4-(6-hydroxy-benzo[d]thiazol-2-yl)but-3-en-1-yn-1-yl)pyrazin-2-yl)(methyl)carbamate (971 mg) produced in Example 1, 2-((tert-butyldimethylsilyl)oxy)-3-hydroxypropyl 4-methyl-benzenesulfonate (1.11 g) produced in Reference Example 15, and bis(2-methoxyethyl) azodicarboxylate (835 mg).

$^1$H NMR (300 MHz, DMSO-$d_6$) δ 0.04 (3H, s), 0.04 (3H, s), 0.81 (9H, s), 1.51 (9H, s), 2.38 (3H, s), 3.34 (3H, s), 3.90-4.19 (4H, m), 4.20-4.32 (1H, m), 7.02 (1H, d, J=16.0 Hz), 7.02-7.08 (1H, m), 7.45 (2H, brd, J=8.1 Hz), 7.48 (1H, brd, J=16.0 Hz), 7.66 (1H, d, J=2.3 Hz), 7.79 (2H, d, J=8.3 Hz), 7.91 (1H, d, J=9.0 Hz), 8.65 (1H, d, J=1.5 Hz), 9.06 (1H, d, J=1.5 Hz)

Reference Example 24: Production of tert-butyl (E)-(5-(4-(6-(3-fluoro-2-hydroxypropoxy)benzo[d]thiazol-2-yl)but-3-en-1-yn-1-yl)pyrimidin-2-yl)(methyl)carbamate

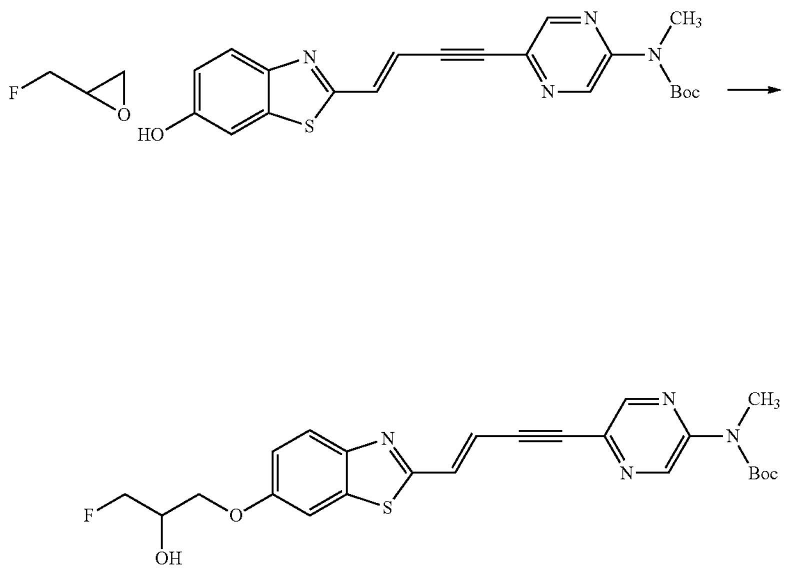

To a solution of tert-butyl (E)-(5-(4-(6-hydroxybenzo[d]thiazol-2-yl)but-3-en-1-yn-1-yl)pyrimidin-2-yl)(methyl) carbamate (99 mg) produced in Example 2 and potassium carbonate (66 mg) in DMF (3 ml), was added 2-(fluoromethyl)oxirane (CAS [503-09-3]) (0.060 ml) at room temperature. The mixture was heated at 80° C. for 4 h, cooled to room temperature, diluted with water and ethyl acetate, neutralized with 5% citric acid solution, and extracted with ethyl acetate. The extract was washed with water and brine, dried over anhydrous sodium sulfate, and concentrated under reduced pressure. The residue was purified by silica gel column chromatography (hexane/ethyl acetate) to obtain the title compound (36 mg) as a yellow solid.

$^1$H NMR (300 MHz, DMSO-$d_6$) δ 1.46 (9H, s), 3.34 (3H, s), 4.02-4.16 (3H, m), 4.39-4.46 (1H, m), 4.56-4.63 (1H, m), 5.49 (1H, d, J=5.3 Hz), 6.99 (1H, d, J=16.2 Hz), 7.16 (1H, dd, J=9.0, 2.6 Hz), 7.41 (1H, d, J=16.2 Hz), 7.73 (1H, d, J=2.3 Hz), 7.91 (1H, d, J=9.0 Hz), 8.87 (2H, s)

Reference Example 25: Production of (E)-3-((2-(4-(5-((tert-butoxycarbonyl)(methyl)amino)pyrazin-2-yl)but-1-en-3-yn-1-yl)benzo[d]thiazol-6-yl)oxy)-2-hydroxypropyl 4-methylbenzenesulfonate

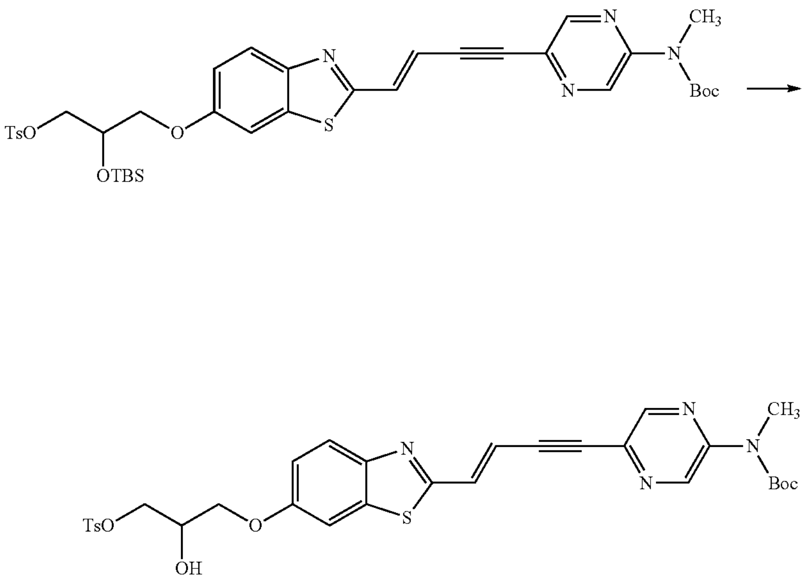

To a solution of (E)-3-((2-(4-(5-((tert-butoxycarbonyl)(methyl)amino)pyrazin-2-yl)but-1-en-3-yn-1-yl)benzo[d]thiazol-6-yl)oxy)-2-((tert-butyldimethylsilyl)oxy)propyl 4-methylbenzenesulfonate (100 mg) produced in Reference Example 23 and acetic acid (0.023 ml) in THF (10 ml) was added tetra-n-butylammonium fluoride (1M THF solution, 0.533 ml) at 0° C. The mixture was stirred at 0° C. for 0.5 h, diluted with water, and extracted with ethyl acetate. The extract was washed with water and brine, dried over anhydrous sodium sulfate, and concentrated under reduced pressure. The residue was purified by silica gel column chromatography (hexane/ethyl acetate) to obtain the title compound (37 mg) as a yellow solid.

$^1$H NMR (300 MHz, DMSO-$d_6$) δ 1.51 (9H, s), 2.35 (3H, s), 3.34 (3H, s), 3.91-4.19 (5H, m), 5.59 (1H, d, J=4.9 Hz), 7.02 (1H, d, J=16.1 Hz), 7.00-7.07 (1H, m), 7.35-7.43 (2H, m), 7.48 (1H, d, J=16.1 Hz), 7.62 (1H, d, J=2.5 Hz), 7.77 (2H, d, J=8.3 Hz), 7.89 (1H, d, J=9.0 Hz), 8.65 (1H, d, J=1.5 Hz), 9.06 (1H, d, J=1.5 Hz)

Reference Example 26: Production of (E)-2-hydroxy-3-((2-(4-(5-(methylamino)pyrazin-2-yl)but-1-en-3-yn-1-yl)benzo[d]thiazol-6-yl)oxy)propyl 4-methylbenzenesulfonate

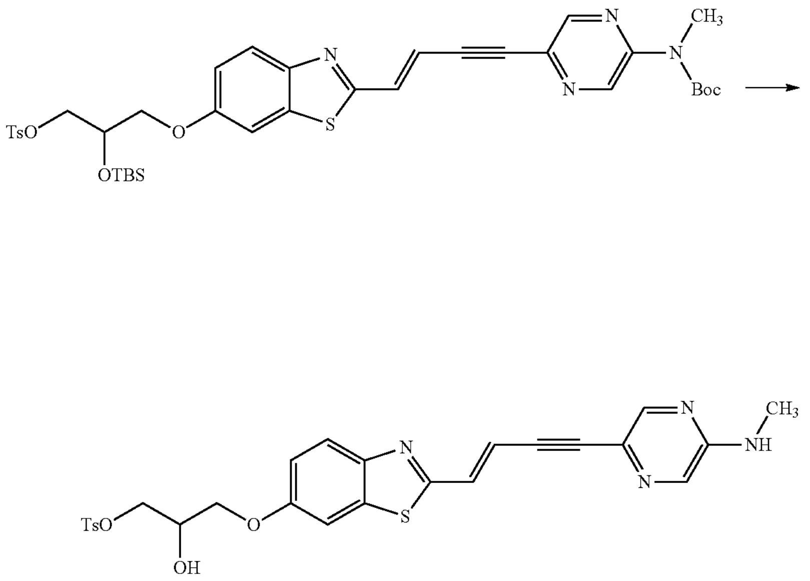

A solution of (E)-3-((2-(4-(5-((tert-butoxycarbonyl)(methyl)amino)pyrazin-2-yl)but-1-en-3-yn-1-yl)benzo[d]thiazol-6-yl)oxy)-2-((tert-butyldimethylsilyl)oxy)propyl 4-methylbenzenesulfonate (750 mg) produced in Reference Example 23 in TFA (13.5 ml) and water (1.5 ml) was stirred at room temperature for 0.5 h, cooled to 0° C., diluted with ethyl acetate, neutralized with saturated sodium bicarbonate solution, and extracted with ethyl acetate. The extract was washed with water and brine. The solid precipitated from the extract was collected by filtration. The filtrate was dried over anhydrous sodium sulfate, and then concentrated under reduced pressure. The residual solid and the solid collected by the filtration were combined and suspended in hexane, collected by filtration, washed with hexane, and dried to obtain the title compound (550 mg) as a yellow solid.

$^1$H NMR (400 MHz, DMSO-$d_6$) δ 2.34 (3H, s), 2.84 (3H, d, J=4.8 Hz), 3.90-3.98 (2H, m), 4.02-4.17 (3H, m), 5.60 (1H, d, J=4.8 Hz), 6.95 (1H, d, J=16.0 Hz), 7.00 (1H, dd, J=8.8, 2.4 Hz), 7.29 (1H, d, J=16.0 Hz), 7.40 (2H, d, J=8.0 Hz), 7.59 (1H, d, J=2.4 Hz), 7.68 (1H, brs), 7.77 (2H, d, J=8.4 Hz), 7.86 (1H, d, J=8.8 Hz), 7.94 (1H, d, J=1.6 Hz), 8.21 (1H, d, J=1.2 Hz)

Example 3: Production of (E)-2-(4-(5-(methylamino) pyrazin-2-yl) but-1-en-3-yn-1-yl)benzo[d]thiazol-6-ol

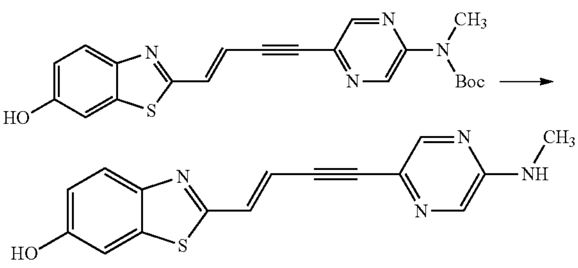

A solution of tert-butyl (E)-(5-(4-(6-hydroxybenzo[d]thiazol-2-yl)but-3-en-1-yn-1-yl)pyrazin-2-yl)(methyl)carbamate (230 mg) produced in Example 1 in TFA (4 ml) was stirred at room temperature for 1 h, and concentrated under reduced pressure. Ethyl acetate was added to the residue. The mixture was cooled to 0° C., neutralized with saturated sodium bicarbonate solution, and extracted with ethyl acetate. The extract was washed with water and brine, dried over anhydrous sodium sulfate, and concentrated under reduced pressure. The residual solid was suspended in ethyl acetate, collected by filtration, washed with ethyl acetate, and dried to obtain the title compound (140 mg) as a yellow solid.

$^1$H NMR (300 MHz, DMSO-$d_6$) δ 2.84 (3H, d, J=4.9 Hz), 6.81-6.92 (1H, m), 6.98 (1H, dd, J=8.8, 2.4 Hz), 7.26 (1H, d, J=15.8 Hz), 7.37 (1H, d, J=2.3 Hz), 7.63 (1H, q, J=5.0 Hz), 7.79 (1H, d, J=8.7 Hz), 7.94 (1H, d, J=1.5 Hz), 8.20 (1H, d, J=1.1 Hz), 9.97 (1H, s)

Example 4: Production of (E)-1-fluoro-3-((2-(4-(5-(methylamino) pyrazin-2-yl) but-1-en-3-yn-1-yl) benzo[d]thiazol-6-yl)oxy)propan-2-ol (hereinafter referred to as "SPAL-T-06")

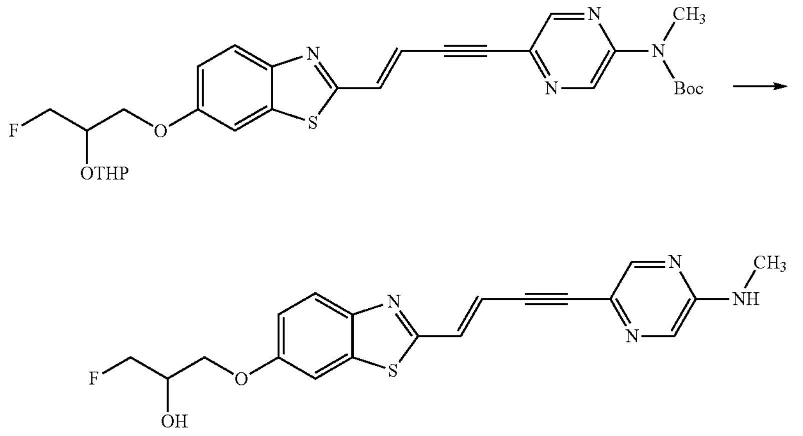

A solution of tert-butyl (E)-(5-(4-(6-(3-fluoro-2-((tetrahydro-2H-pyran-2-yl)oxy)propoxy)benzo[d]thiazol-2-yl) but-3-en-1-yn-1-yl)pyrazin-2-yl)(methyl)carbamate (2.06 g) produced in Reference Example 20 in TFA (20 ml) was stirred at room temperature for 0.5 h and concentrated under reduced pressure. Toluene was added to the residue. The mixture was concentrated under reduced pressure. Then, ethyl acetate and water were added to the residue. The mixture was neutralized with 5% sodium bicarbonate solution. The precipitated solid was collected by filtration, washed with water and ethyl acetate, and dried. The filtrate and the washing liquid were combined and extracted with ethyl acetate. The extract was washed with water and brine, dried over anhydrous sodium sulfate, and concentrated under reduced pressure. The residual solid was suspended in ethyl acetate, collected by filtration, washed with ethyl acetate, and dried. This solid and the solid obtained before the extraction were combined, suspended in ethyl acetate, collected by filtration, washed with ethyl acetate, and dried to obtain the title compound (1.07 g) as a yellow solid.

$^1$H NMR (300 MHz, DMSO-$d_6$) δ 2.84 (3H, d, J=4.9 Hz), 4.00-4.16 (3H, m), 4.37-4.49 (1H, m), 4.53-4.66 (1H, m), 5.51 (1H, d, J=5.1 Hz), 6.95 (1H, d, J=16.0 Hz), 7.15 (1H, dd, J=9.0, 2.6 Hz), 7.29 (1H, d, J=16.0 Hz), 7.67 (1H, q, J=4.6 Hz), 7.71 (1H, d, J=2.6 Hz), 7.89 (1H, d, J=9.0 Hz), 7.94 (1H, d, J=1.5 Hz), 8.21 (1H, d, J=1.3 Hz)

Example 5: Production of (R,E)-1-fluoro-3-((2-(4-(5-(methylamino) pyrazin-2-yl) but-1-en-3-yn-1-yl) benzo[d]thiazol-6-yl)oxy) propan-2-ol

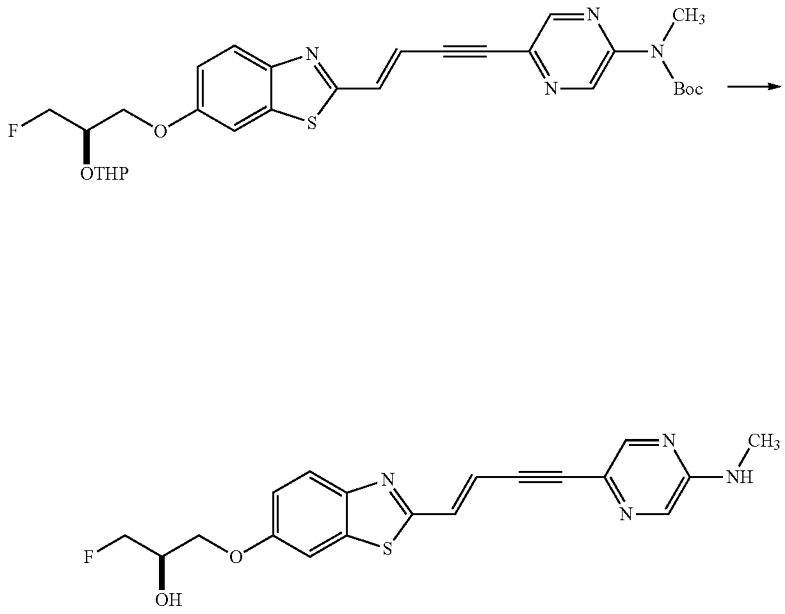

The title compound (58 mg) was obtained as a pale-yellow solid, in a manner similar to that in Example 4 with use of tert-butyl (5-((E)-4-(6-((2R)-3-fluoro-2-((tetrahydro-2H-pyran-2-yl)oxy)propoxy)benzo[d]thiazol-2-yl)but-3-en-1-yn-1-yl)pyrazin-2-yl)(methyl)carbamate (98 mg) produced in Reference Example 21.

$^1$H NMR (300 MHz, DMSO-$d_6$) δ 2.84 (3H, d, J=4.8 Hz), 4.01-4.17 (3H, m), 4.37-4.49 (1H, m), 4.53-4.65 (1H, m), 5.50 (1H, d, J=5.1 Hz), 6.95 (1H, d, J=16.1 Hz), 7.15 (1H, dd, J=8.9, 2.6 Hz), 7.29 (1H, d, J=16.1 Hz), 7.66 (1H, q, J=4.9 Hz), 7.71 (1H, d, J=2.5 Hz), 7.89 (1H, d, J=9.0 Hz), 7.94 (1H, d, J=1.4 Hz), 8.21 (1H, d, J=1.3 Hz)

Example 6: Production of (S,E)-1-fluoro-3-((2-(4-(5-(methylamino) pyrazin-2-yl) but-1-en-3-yn-1-yl) benzo[d]thiazol-6-yl)oxy) propan-2-ol

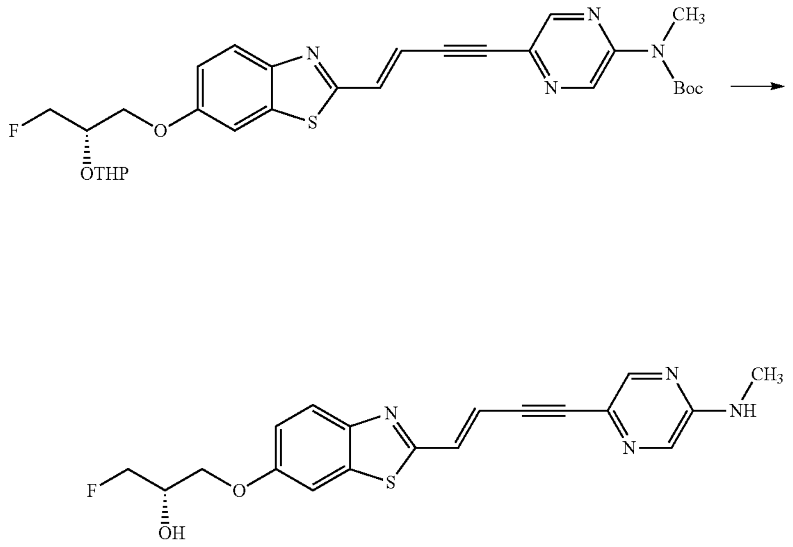

The title compound (12 mg) was obtained as a pale-yellow solid, in a manner similar to that in Example 4 with use of tert-butyl (5-((E)-4-(6-((2S)-3-fluoro-2-((tetrahydro-2H-pyran-2-yl)oxy)propoxy)benzo[d]thiazol-2-yl)but-3-en-1-yn-1-yl)pyrazin-2-yl)(methyl)carbamate (20 mg) produced in Reference Example 22.

$^1$H NMR (300 MHz, DMSO-$d_6$) δ 2.84 (3H, d, J=4.7 Hz), 4.00-4.17 (3H, m), 4.37-4.49 (1H, m), 4.53-4.65 (1H, m), 5.51 (1H, d, J=4.7 Hz), 6.95 (1H, d, J=16.0 Hz), 7.15 (1H, dd, J=8.9, 2.5 Hz), 7.29 (1H, d, J=16.2 Hz), 7.62-7.70 (1H, m), 7.71 (1H, d, J=2.4 Hz), 7.89 (1H, d, J=8.9 Hz), 7.94 (1H, d, J=1.3 Hz), 8.21 (1H, d, J=1.1 Hz)

Example 7: Production of (E)-1-fluoro-3-((2-(4-(2-(methylamino)pyrimidin-5-yl)but-1-en-3-yn-1-yl) benzo[d]thiazol-6-yl)oxy)propan-2-ol (hereinafter referred to as "SPAL-T-05")

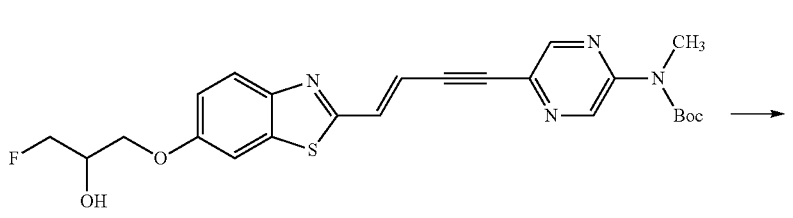

-continued

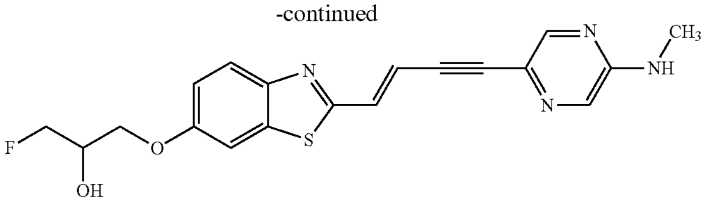

The title compound (15 mg) was obtained as a yellow solid, in a manner similar to that in Example 4 with use of tert-butyl (E)-(5-(4-(6-(3-fluoro-2-hydroxypropoxy)benzo[d]thiazol-2-yl)but-3-en-1-yn-1-yl)pyrimidin-2-yl)(methyl)carbamate (34 mg) produced in Reference Example 24.

$^1$H NMR (300 MHz, DMSO-$d_6$) δ 2.84 (3H, d, J=4.5 Hz), 4.00-4.16 (3H, m), 4.36-4.50 (1H, m), 4.52-4.66 (1H, m), 5.49 (1H, d, J=5.3 Hz), 6.86-6.99 (1H, m), 7.10-7.18 (1H, m), 7.25 (1H, d, J=15.8 Hz), 7.67-7.77 (2H, m), 7.88 (1H, d, J=9.0 Hz), 8.38-8.58 (2H, m)

Example 8: Production of (E)-3-((2-(4-(5-((tert-butoxycarbonyl)(methyl)amino)pyrazin-2-yl)but-1-en-3-yn-1-yl)benzo[d]thiazol-6-yl)oxy)-2-((tetrahydro-2H-pyran-2-yl)oxy)propyl 4-methylbenzenesulfonate

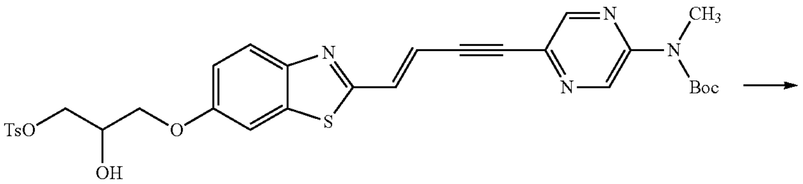

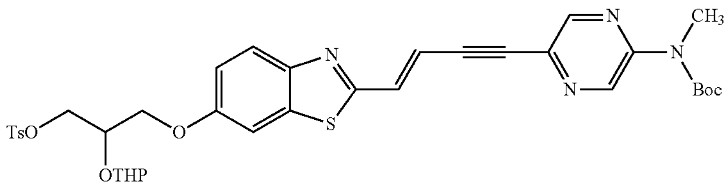

To a solution of (E)-3-((2-(4-(5-((tert-butoxycarbonyl)(methyl)amino)pyrazin-2-yl)but-1-en-3-yn-1-yl)benzo[d]thiazol-6-yl)oxy)-2-hydroxypropyl 4-methylbenzenesulfonate (35 mg) produced in Reference Example 25 and 3,4-dihydro-2H-pyrane (0.050 ml) in THF (15 ml), was added p-toluenesulfonic acid monohydrate (21 mg) at room temperature. The mixture was stirred at room temperature for 4 h. Then, 3,4-dihydro-2H-pyrane (0.249 ml) and p-toluenesulfonic acid monohydrate (21 mg) were added to the mixture at room temperature. The mixture was stirred at room temperature overnight, diluted with ethyl acetate, neutralized with 5% sodium bicarbonate solution, diluted with water, and extracted with ethyl acetate. The extract was washed with water and brine, dried over anhydrous sodium sulfate, and concentrated under reduced pressure. The residue was purified by silica gel column chromatography (hexane/ethyl acetate). The desired fractions containing the desired compound were concentrated under reduced pressure. The residual solid was suspended in hexane, collected by filtration, washed with hexane, and dried to obtain the title compound (28 mg) as a yellow solid.

$^1$H NMR (300 MHz, DMSO-$d_6$) δ 1.32-1.72 (15H, m), 2.35 (3H, s), 3.34-3.46 (4H, m), 3.61-3.93 (1H, m), 4.01-4.41 (5H, m), 4.66-4.90 (1H, m), 6.99-7.05 (1H, m), 7.02-7.09 (1H, m), 7.41 (2H, brd, J=8.1 Hz), 7.48 (1H, d, J=16.2 Hz), 7.65 (1H, d, J=2.1 Hz), 7.79 (2H, brd, J=7.3 Hz), 7.90 (1H, d, J=8.9 Hz), 8.65 (1H, d, J=1.1 Hz), 9.06 (1H, d, J=0.9 Hz).

Example 9: Production of (E)-3-((2-(4-(5-(methylamino) pyrazin-2-yl) but-1-en-3-yn-1-yl)benzo[d]thiazol-6-yl)oxy)-2-((tetrahydro-2H-pyran-2-yl)oxy)propyl 4-methylbenzenesulfonate

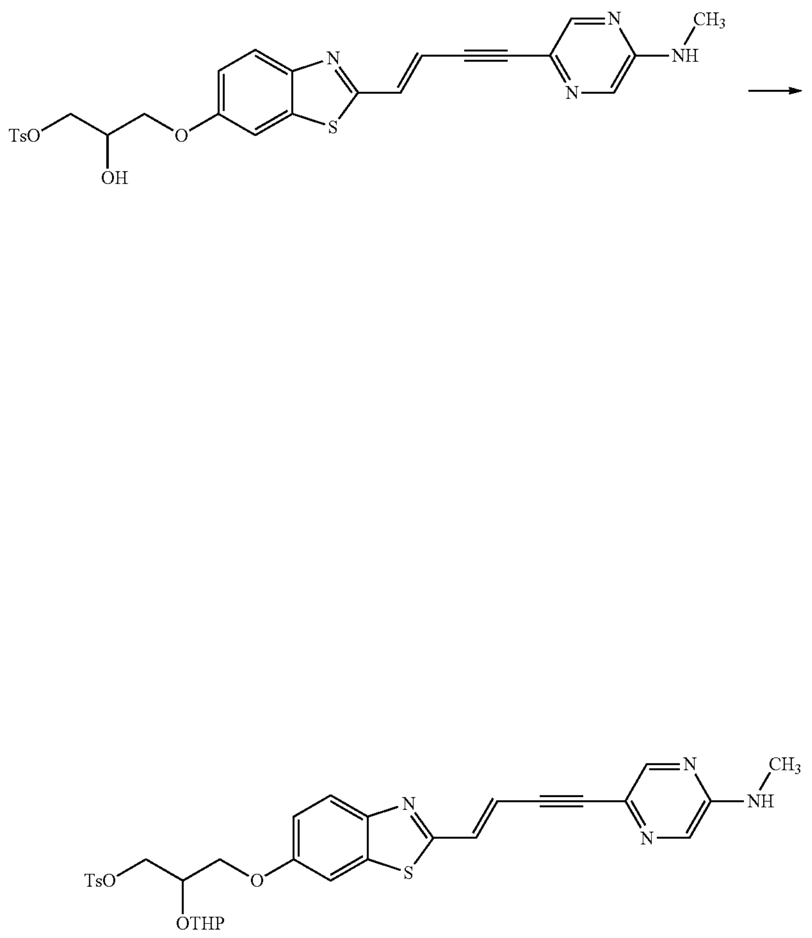

To a solution of (E)-2-hydroxy-3-((2-(4-(5-(methylamino) pyrazin-2-yl) but-1-en-3-yn-1-yl)benzo[d]thiazol-6-yl)oxy) propyl 4-methylbenzenesulfonate (35 mg) produced in Reference Example 26 and 3,4-dihydro-2H-pyrane (0.018 ml) in THF (15 ml), was added p-toluenesulfonic acid monohydrate (12 mg) at room temperature. The mixture was stirred at room temperature for 0.5 h. Then, 3,4-dihydro-2H-pyrane (0.159 ml), p-toluenesulfonic acid monohydrate (24 mg), and DMF (5 ml) were added to the mixture at room temperature. The mixture was stirred at room temperature overnight, diluted with water, and extracted with ethyl acetate. The extract was washed with water and brine, dried over anhydrous sodium sulfate, and concentrated under reduced pressure. The residue was purified by silica gel column chromatography (hexane/ethyl acetate). The fractions containing the desired compound were concentrated under reduced pressure. The residual solid was suspended in hexane, collected by filtration, washed with hexane, and dried to obtain the title compound (21 mg) as a yellow solid.

$^{1}H$ NMR (300 MHz, DMSO-$d_6$) δ 1.32-1.71 (6H, m), 2.35 (3H, s), 2.84 (3H, d, J=4.9 Hz), 3.35-3.46 (1H, m), 3.62-3.87 (1H, m), 4.05-4.19 (3H, m), 4.20-4.36 (2H, m), 4.65-4.87 (1H, m), 6.96 (1H, d, J=16.2 Hz), 7.02 (1H, dd, J=8.9, 1.6 Hz), 7.30 (1H, d, J=16.0 Hz), 7.41 (2H, d, J=7.9 Hz), 7.62 (1H, d, J=2.6 Hz), 7.67 (1H, q, J=4.4 Hz), 7.79 (2H, dd, J=8.4, 1.6 Hz), 7.86 (1H, d, J=9.0 Hz), 7.94 (1H, d, J=1.5 Hz), 8.21 (1H, d, J=1.3 Hz)

Example 10: Production Example 1 of [$^{18}F$]SPAL-T-06

By the following scheme, SPAL-T-06 in which a fluorine atom was $^{18}F$ (hereinafter referred to as [$^{18}F$]SPAL-T-06) was produced.

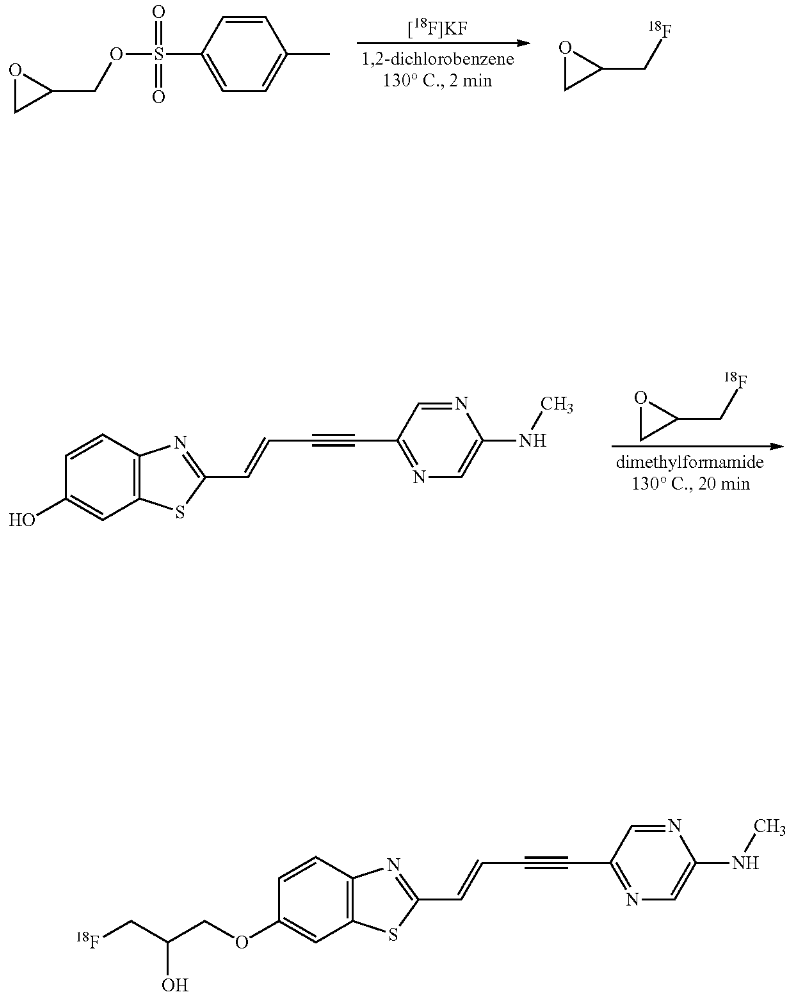

[18F]epifluorohydrin was synthesized by (i) nucleophilic substitution of glycidyl tosylate with use of [18F]fluoride ions and (ii) purification by distillation. The following reaction was carried out under dim light. [18F]epifluorohydrin, a DMF (250 μl) solution containing (E)-2-(4-(5-(methylamino)pyrazine-2-yl)but-1-en-3-yn-1-yl)benzo[d]thiazol-6-ol (2 mg) produced in Example 3, and a 1M aqueous sodium hydroxide solution (6.5 μl) were introduced into a reaction vessel. A reaction mixture was heated at 130° C. for 20 minutes. After the reaction vessel was cooled, an HPLC solvent (500 μl) to be used for the subsequent HPLC was introduced into the reaction vessel. A mixed solution thus obtained was purified by HPLC (HPLC: CAPCELL PAK C18 UG80 10 mm×250 mm, acetonitrile/water=4/6 (containing 0.1% triethylamine), 5 ml/minute). A fraction corresponding to [18F]SPAL-T-06 was collected in a flask containing ethanol (300 μl), 25% ascorbic acid (100 μl), and Tween80 (75 μl). Then, a solvent was evaporated under reduced pressure. A residue was dissolved in physiological saline (3 ml, pH 7.4) to obtain [18F]SPAL-T-06 as an injection solution.

Example 11: Production Example 2 of [18F]SPAL-T-06

By the following scheme, [18F]SPAL-T-06 was produced.

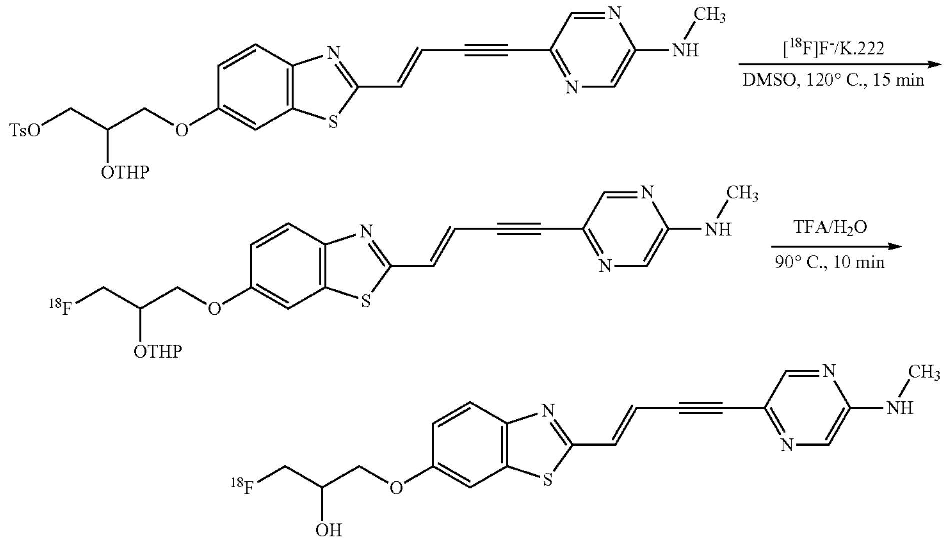

[18F]fluoride ions were eluted with a 50% acetonitrile solution (0.4 ml) containing K.222 (Kryptofix 222) (7.5 mg) and potassium carbonate (2.77 mg). A resulting solution was introduced into a reaction vessel, and then heated under a nitrogen gas flow to dry and solidify a solvent. Subsequently, anhydrous acetonitrile (0.1 ml) was added to the reaction vessel. The solvent was azeotropically evaporated, and the inside of the reaction vessel was sufficiently dried. The following reaction was carried out under dim light. A DMSO (300 μl) solution containing (E)-3-((2-(4-(5-(methylamino) pyrazin-2-yl) but-1-en-3-yn-1-yl)benzo[d]thiazol-6-yl)oxy)-2-((tetrahydro-2H-pyran-2-yl)oxy)propyl 4-methylbenzenesulfonate (2 mg) produced in Example 9 was introduced into the reaction vessel. A reaction mixture was heated at 120° C. for 15 minutes. After the reaction vessel was cooled, TFA/water (600 μl) was added to carry out hydrolysis at 90° C. for 10 minutes. After the reaction vessel was cooled, an aqueous 4N sodium acetate solution (1 ml) was added to the reaction vessel, and a mixture thus obtained was stirred. A mixed solution thus obtained was purified by HPLC (HPLC: CAPCELL PAK C18 UG80 10 mm×250 mm, acetonitrile/water=4/6 (containing 0.1% triethylamine), 5 ml/minute). A fraction corresponding to [18F]SPAL-T-06 was collected in a flask containing ethanol (300 μl), 25% ascorbic acid (100 μl), and Tween80 (75 μl). Then, a solvent was evaporated under reduced pressure. A residue was dissolved in physiological saline (3 ml, pH 7.4) to obtain [18F]SPAL-T-06 as an injection solution.

[Optical Imaging of Human Brain]

(Dissected Brain Tissue)

Postmortem human brains were obtained in autopsies carried out with respect to a patient with dementia with Lewy bodies (DLB) and a patient with Alzheimer's disease (AD). In a cryostat (HM560, Carl Zeiss), frozen tissue from the DLB patient was sliced into sections each having a thickness of 20 μm. Brain tissue from the AD patient was fixed in 10% neutral buffered formalin, embedded in a paraffin block, and sliced into sections each having a thickness of 6 μm.

(In Vitro Fluorescence Microscope Measurement)

Figure 2:
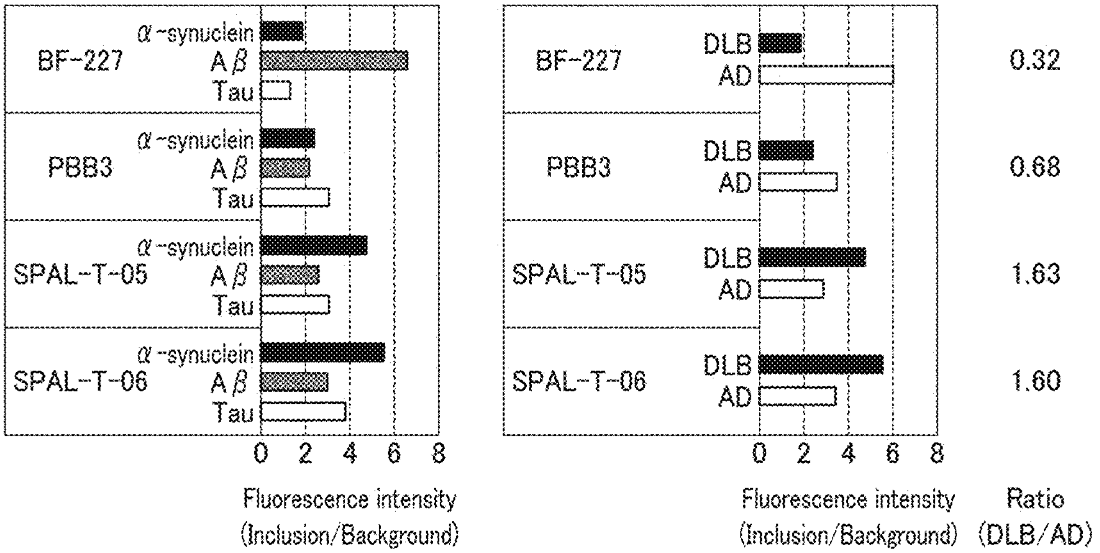
FIG. 2 is a diagram showing results of quantifying fluorescence in lesion-enriched areas and lesion-free areas.

Postfixed fresh frozen sections of amygdala tissue obtained from the brain of the DLB patient and deparaffinized sections of formalin-fixed paraffin-embedded middle frontal gyrus tissue obtained from the brain of the AD patient were used. Each brain section and a 30 μM test compound were incubated in a 50% ethanol solution at room temperature for 30 minutes. Thereafter, the section was washed with a 50% ethanol solution for 5 minutes and with ultrapure water for 3 minutes. This washing was carried out twice. After the section was mounted in a mounting medium (VECTASHIELD H-1000, Vector Laboratories), an image of a lesion-enriched area on the section was obtained with use of a fluorescence microscope (DM4000, Leica, excitation wavelength: 391 nm to 437 nm). Fluorescence images are shown in FIG. 1. In FIG. 1, each arrowhead indicates fluorescence from the compound binding to α-synuclein aggregates in the brain of the DLB patient, each arrow indicates fluorescence from the compound binding to amyloid-β aggregates in the brain of the AD patient, and an asterisk indicates fluorescence from the compound binding to tau aggregates in the brain of the AD patient. The fluorescence intensities of lesion-enriched areas and lesion-free areas (background) were quantified with use of analysis software (Image J). Results are shown in FIG. 2. Note that SPAL-T-05 and SPAL-T-06 were each used as the test compound. Note also that BF-227 (2-(2-[2-dimethylaminothiazol-5-yl]ethenyl)-6-(2-[fluoro]ethoxy)benzoxazole (catalog No.: NP039-0)) and PBB3 (2-((1E,3E)-4-(6-(methylamino)pyridin-3-yl)buta-1,3-dienyl)benzo[d]thiazol-6-ol) (catalog No.: NP039-0), each available from NARD INSTITUTE, LTD., were each used as a control compound.

As shown in FIGS. 1 and 2, it was found that SPAL-T-06 and SPAL-T-05 each bound to, with reactivity greater than that of PBB3, α-synuclein aggregates formed in the brain of the DLB patient. It was also found that binding of each of SPAL-T-06 and SPAL-T-05 to the α-synuclein aggregates was greater than binding of each of SPAL-T-06 and SPAL-T-05 to tau aggregates or amyloid-β aggregates formed in the brain of the AD patient. That is, it was indicated that the compound in accordance with an embodiment of the present invention had high binding selectivity with respect to α-synuclein aggregates. Note that in vitro fluorescence microscope measurement was carried out with respect to the brain of a patient with multiple system atrophy (MSA) in a manner similar to that with respect to the brain of the DLB patient, and similar results were obtained.

Note that it was found that BF-227, which was reported as a PET probe for an α-synuclein lesion, mainly bound to the amyloid-β aggregates in the AD patient and binding of BF-227 to the α-synuclein aggregates was weaker than that of each of SPAL-T-06 and SPAL-T-05 to the α-synuclein aggregates. That is, it was indicated that BF-227 had low binding selectivity with respect to α-synuclein aggregates.

[Optical Imaging of Mouse Brain]

(Preparation of α-Synuclein Fibril-Inoculated Mouse Model)

When mouse α-synuclein is expressed in and extracted from *E. coli* as a recombinant protein and then incubated in vitro, insoluble α-synuclein aggregates are formed. By inoculating these α-synuclein aggregates into the striatum of a mouse, the α-synuclein aggregates propagate to surrounding areas via the neural circuitry, and an α-synuclein lesion is observed in the cerebral neocortex several months later (Masuda-Suzukake et al. Acta Neuropathol Commun 2, 88, 2014; Shimozawa et al. Acta Neuropathol Commun 5, 12, 2017). By extracting the brain of this mouse, preparing a section, and then analyzing the section by fluorescent staining, it is possible to examine whether the compound in accordance with an embodiment of the present invention binds to a lesion caused by phosphorylated α-synuclein.

(Preparation of α-Synuclein Fibril-Inoculated Mouse Model)

First, mouse α-synuclein was expressed in and extracted from *E. coli* as a recombinant protein, and then incubated in vitro to form insoluble α-synuclein aggregates. The α-synuclein aggregates were then inoculated into the striatum of a mouse. The α-synuclein aggregates propagated to surrounding areas via the neural circuitry, and α-synuclein lesions were observed in the cerebral neocortex several months later. Note that the inoculation of the α-synuclein aggregates into the striatum of the mouse was carried out in the following manner. First, hair on the head of a 9-week-old C57/BL/6 male mouse which had been anesthetized with 1.5% (v/v) isoflurane was removed, and the scalp was disinfected with isodine, followed by application of xylocaine and incision in the scalp to expose the skull. Then, a hole was drilled in the skull at a position of 0.05 mm posterior to the bregma and 2 mm lateral to the midline, and 3 μl of an α-synuclein fibril solution (mouse α-synuclein fibril (4 mg/ml) in saline) was injected into a position 2 μm ventral to the brain surface with use of a glass pipette. The scalp was then returned and sutured.

(In Vitro Fluorescence Microscope Measurement)

Figure 3:
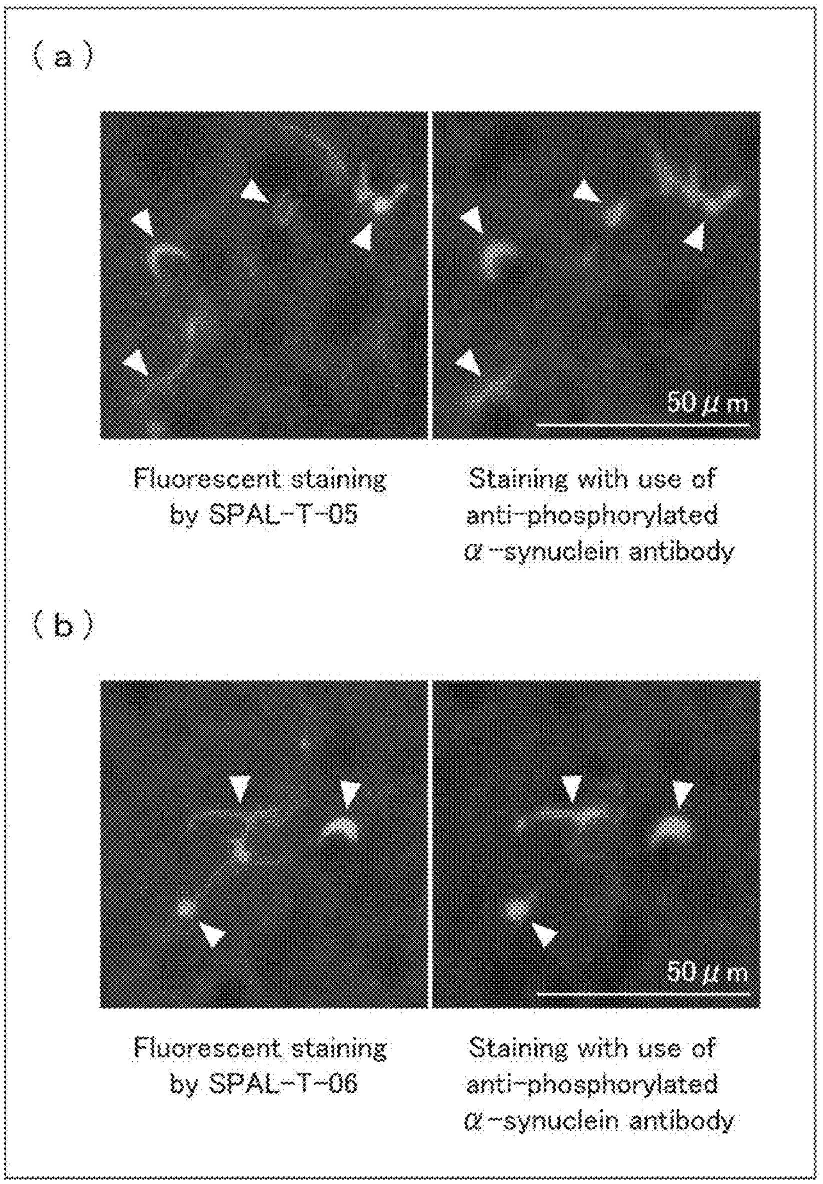
FIG. 3 is a diagram showing results of fluorescence microscope measurement of an α-synuclein fibril-inoculated mouse.

The brain of this α-synuclein fibril-inoculated mouse was extracted, and then sections were prepared. The sections were analyzed by fluorescent staining. Specifically, each brain section of the α-synuclein fibril-inoculated mouse and a 30 μM compound were incubated in a 20% ethanol solution at room temperature for 30 minutes. Thereafter, the section was washed with a 20% ethanol solution for 5 minutes and with ultrapure water for 3 minutes. This washing was carried out twice. After the section was mounted in a mounting medium (VECTASHIELD H-1000), an image of an α-synuclein aggregate-enriched area on the section was obtained with use of a fluorescence microscope (DM4000 (excitation wavelength: 391 nm to 437 nm)). The same section was washed with a phosphate buffer solution, and then treated in an autoclave for antigen retrieval. After the section was subjected to immunohistochemical staining with use of an anti-phosphorylated α-synuclein monoclonal antibody (pS129, abcam, ab59264) (1:1000) and then mounted in a mounting medium (VECTASHIELD H-1000), an image of the same area as above was obtained with use of a fluorescence microscope (DM4000 (excitation wavelength: 460 nm to 500 nm)). Results are shown in FIG. 3. (a) of FIG. 3 shows results obtained in relation to SPAL-T-05. (b) of FIG. 3 shows results obtained in relation to SPAL-T-06. In each of (a) and (b) of FIG. 3, a right image shows a section subjected to staining with use of the anti-phosphorylated α-synuclein antibody, and a left image shows the section subjected to fluorescent staining by a corresponding one of SPAL-T-05 and SPAL-T-06. In FIG. 3, each arrowhead indicates a lesion, caused by phosphorylated α-synuclein, in the brain of the α-synuclein fibril-inoculated mouse and fluorescence from the compound binding to the phosphorylated α-synuclein.

From the results shown in FIG. 3, it was indicated that SPAL-T-05 and SPAL-T-06 bound to a lesion caused by phosphorylated α-synuclein.

[In Vivo Two-Photon Laser Scanning Fluorescence Microscopy]

Figure 4:
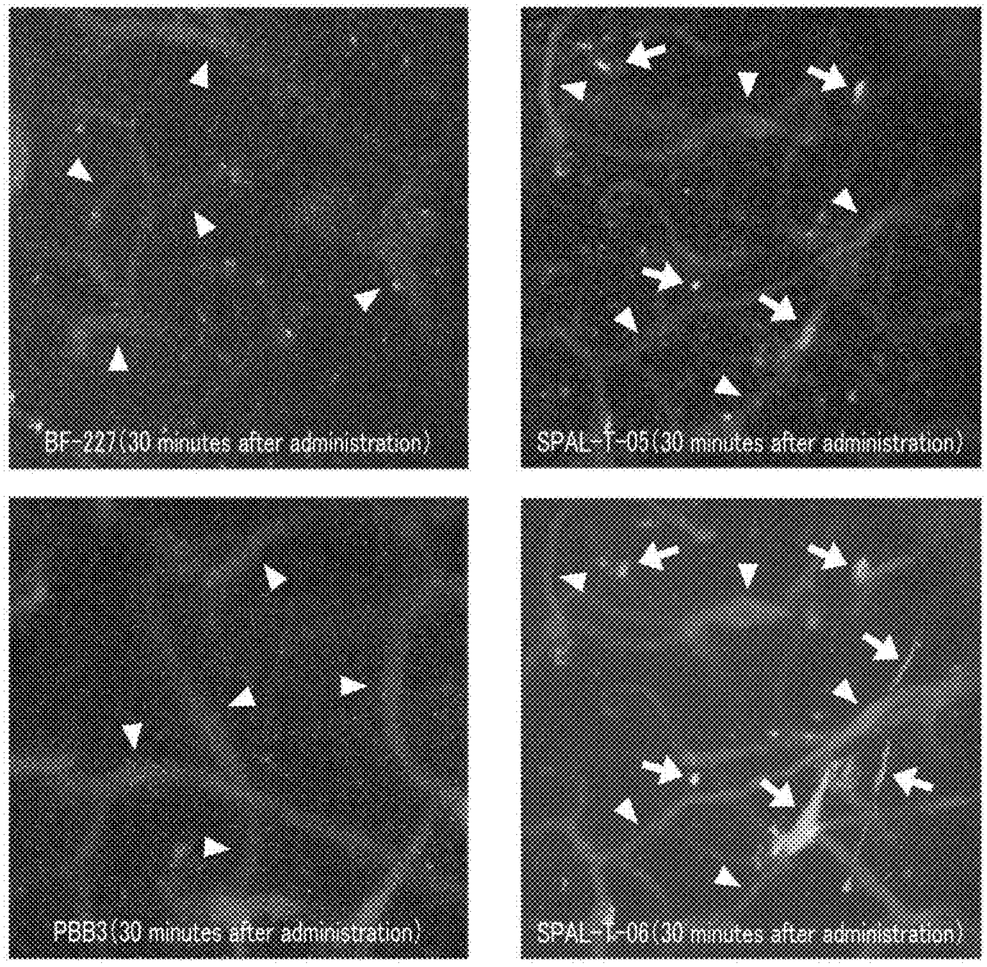
FIG. 4 is a diagram showing results of two-photon laser scanning fluorescence microscopy of a model mouse 6 or more weeks after inoculation of an α-synuclein fibril.

A model mouse was anesthetized with 1.5% (v/v) isoflurane 6 or more weeks after inoculation of an α-synuclein fibril solution. Then, a cranial window was placed on the model mouse in accordance with the Seylaz-Tomita method (Tomita et al. J Cereb Blood Flow Metab 25, 858-67, 2005). Two or more weeks after the placement of the cranial window, the mouse was anesthetized with 1.5% (v/v) isoflurane, and then 50 μl of a DMSO solution containing 0.1% BF-227, PBB3, SPAL-T-05, or SPAL-T-06 was intraperitoneally administered to the mouse. Thirty minutes after the administration, the mouse was fixed under a two-photon laser fluorescence microscope, 100 μl of physiological saline containing 5 mM Sulforhodamine 101 was intraperitoneally administered to the mouse, and then intravital two-photon fluorescence imaging was carried out at an excitation wavelength of 900 nm. Detection wavelengths for BF-227, PBB3, SPAL-T-05, and SPAL-T-06 were set at 500 nm to 550 nm, and a detection wavelength for Sulforhodamine 101 was set at 573 nm to 648 nm. Results are shown in FIG. 4. In FIG. 4, each arrowhead indicates a blood vessel, and each arrow indicates fluorescence from the compound binding to an α-synuclein lesion.

From the results shown in FIG. 4, it was observed by the intravital two-photon laser fluorescence microscope that when each of SPAL-T-05 and SPAL-T-06 was intraperitoneally administered, the compound was delivered into the brain and further into neurons of the living body and bound to α-synuclein lesions. Therefore, it can be said that even in a case where the density or the total number of lesions is low or small and therefore it is difficult to detect the lesions by PET, it is possible to detect the lesions by biofluorescence imaging with use of the compound in accordance with an embodiment of the present invention. In contrast, no α-synuclein lesion was detected even in a case where BF-227 and PBB3 were each intraperitoneally administered and then observation was carried out.

[In Vivo Positron Emission Tomography (PET) Imaging of Mouse Brain]

PET scanning was carried out with use of a micro PET Focus 220 animal scanner (Siemens Medical Solutions), which provided 95 slices each having a thickness of 0.851 mm (center thickness), a 19.0-cm axial field of view (FOV) and a 7.6-cm cross-sectional FOV. Before the scanning, an α-synuclein fibril-inoculated mouse and a physiological saline-injected mouse (control) were each anesthetized with 1.5% (v/v) isoflurane. Emission scanning was carried out in 3D list mode with an energy window of 350 keV to 750 keV for 90 minutes, after intravenous injection of [$^{18}$F]SPAL-T-06 (compound in which SPAL-T-06 was labeled with a positron-emitting radionuclide) (30.1±0.13 MBq). The injection of the radioactive compound and the scanning were carried out under dim light so as to avoid photoisomerization of the compound. The entire list mode data was sorted into 3D sinograms, and then the 3D sinograms were converted into 2D sinograms by Fourier-rebining (frame: 10×1, 6×5, and 5×10 minutes). After the injection of the radioactive compound, summation images during time periods from 0 to 30 minutes, from 30 to 60 minutes, and from 60 to 90 minutes were obtained by maximum a posteriori reconstruction. Moreover, dynamic images were reconstructed by filtered back projection with use of a 0.5-mm Hanning filter. A volume of interest (VOI) was defined for each of the *striata*, the cerebral cortices, and the cerebella with use of PMOD image analysis software (PMOD Technologies), with reference to an MRI template. Results are shown in FIGS. 5 to 7.

Figure 5:
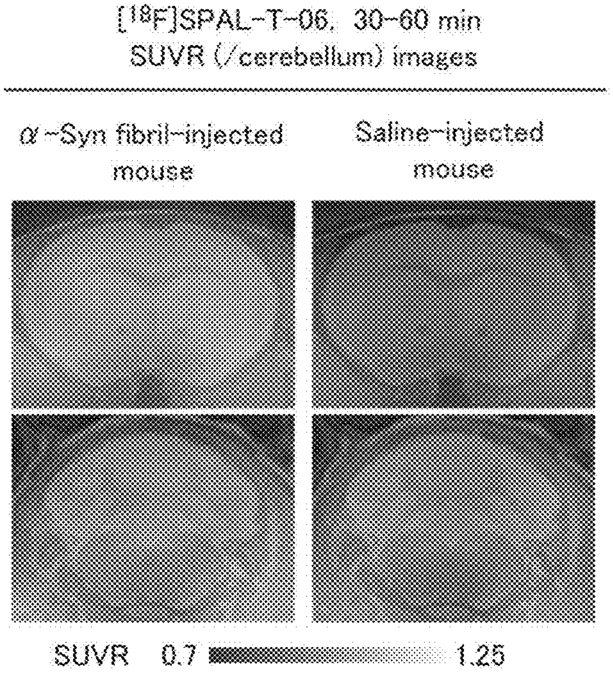
FIG. 5 is a diagram showing results of PET imaging of an α-synuclein fibril-inoculated mouse.

The left images in FIG. 5 show results obtained from the α-synuclein fibril-inoculated mouse 30 to 60 minutes after the intravenous injection of [$^{18}$F]SPAL-T-06. The right images in FIG. 5 show results obtained from the physiological saline-injected mouse. The upper images show coronal sections of the brains which include the *striata*, and the lower images show coronal sections of the brains which include the cerebella. These images are superimposed on standard brain MRI images. FIG. 6 shows time-radioactivity curves obtained from the *striata*, the cerebral cortices, and the cerebella after the intravenous injection of [$^{18}$F]SPAL-T-06. (a) to (d) of FIG. 7 show temporal changes of standardized uptake value ratios (SUVRs) of the *striata* to the cerebella (reference) and SUVRs of the cerebral cortices to the cerebella (reference) after the intravenous injection of [$^{18}$F]SPAL-T-06, and comparisons of the average SUVRs in the α-synuclein fibril-inoculated mouse with those in the physiological saline-injected mouse during the time period from 30 to 60 minutes (n=2, mean±SEMs). (a) of FIG. 7 shows temporal changes of the SUVRs of the *striata* to the cerebella (reference areas) after the intravenous injection of [$^{18}$F]SPAL-T-06. (b) of FIG. 7 shows the average SUVRs of the *striata* (reference areas: cerebella) during the time period from 30 to 60 minutes. (c) of FIG. 7 shows temporal changes of the SUVRs of the cerebral cortices to the cerebella (reference areas) after the intravenous injection of [$^{18}$F]SPAL-T-06. (d) of FIG. 7 shows the average SUVRs of the cerebral cortices (reference areas: cerebella) during the time period from 30 to 60 minutes.

Figure 6:
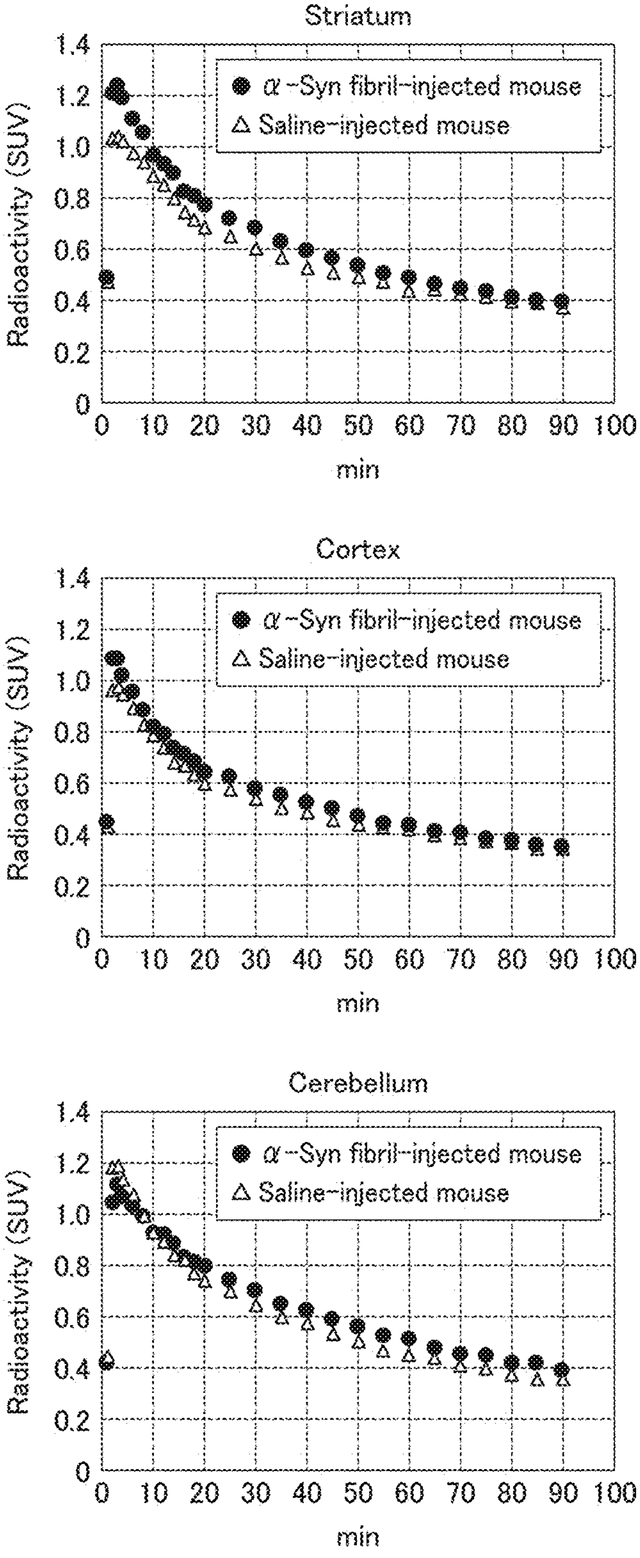
FIG. 6 is a diagram showing results of PET imaging of the α-synuclein fibril-inoculated mouse.
Figure 7:
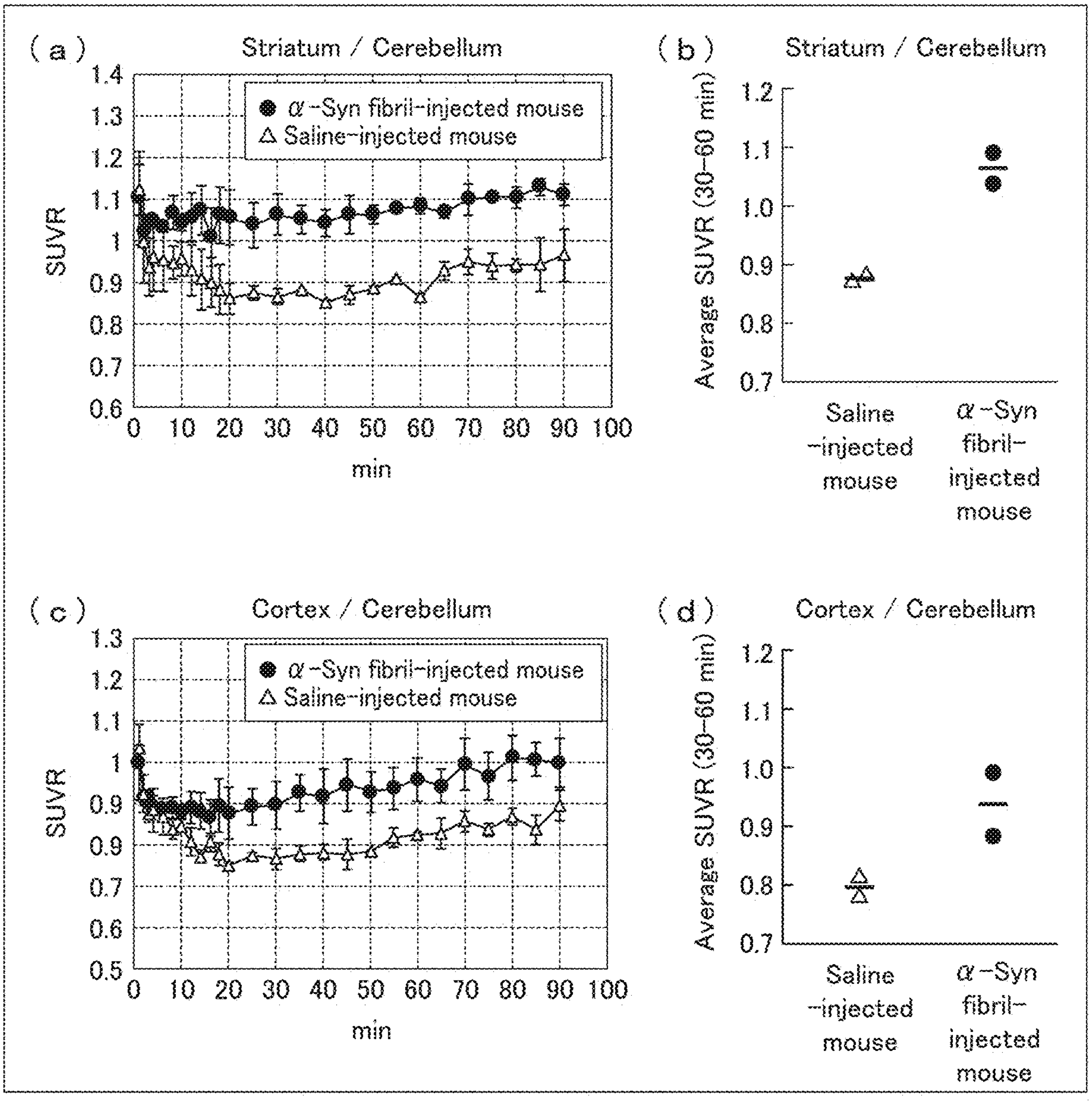
FIG. 7 is a diagram showing results of PET imaging of the α-synuclein fibril-inoculated mouse.

As a result of labeling SPAL-T-06 with the positron-emitting radionuclide, intravenously injecting SPAL-T-06 into the α-synuclein fibril-inoculated model mouse and the physiological saline-injected mouse (control), and then carrying out PET scanning, it became clear that SPAL-T-06 had an adequate brain-entering property or an adequate clearance rate from the brains and exhibited a favorable characteristic as a probe for imaging of α-synuclein aggregates by PET, as shown in FIGS. 5 to 7. Note that, in the α-synuclein fibril-inoculated model mouse, clear accumulation of [$^{18}$F]SPAL-T-06 in the striatum and the cerebral cortex, each of which was rich in α-synuclein lesions, was seen. Thus, it was found that PET scanning with use of [$^{18}$F]SPAL-T-06 enabled imaging of α-synuclein aggregates.

[Ex Vivo Imaging of Mouse Brain]

A physiological saline-injected mouse was anesthetized with 1.5% (v/v) isoflurane. Then, [$^{18}$F]SPAL-T-06 (28.9 MBq) was intravenously injected into the physiological saline-injected mouse. Forty minutes after the administration of [$^{18}$F]SPAL-T-06, the brain was collected and frozen. In a cryostat (HM560), frozen coronal sections each having a thickness of 20 μm and respectively including positions at 0.50 mm, −0.46 mm, −1.94 mm, −3.16 mm, and −6.64 mm from the bregma were prepared. Each section was air-dried, and then placed in contact with an imaging plate for 15 minutes in a cassette. Thereafter, autoradiographs were obtained with use of BAS-5000 (Fuji Film). Results are shown in FIG. 8.

Figure 8:
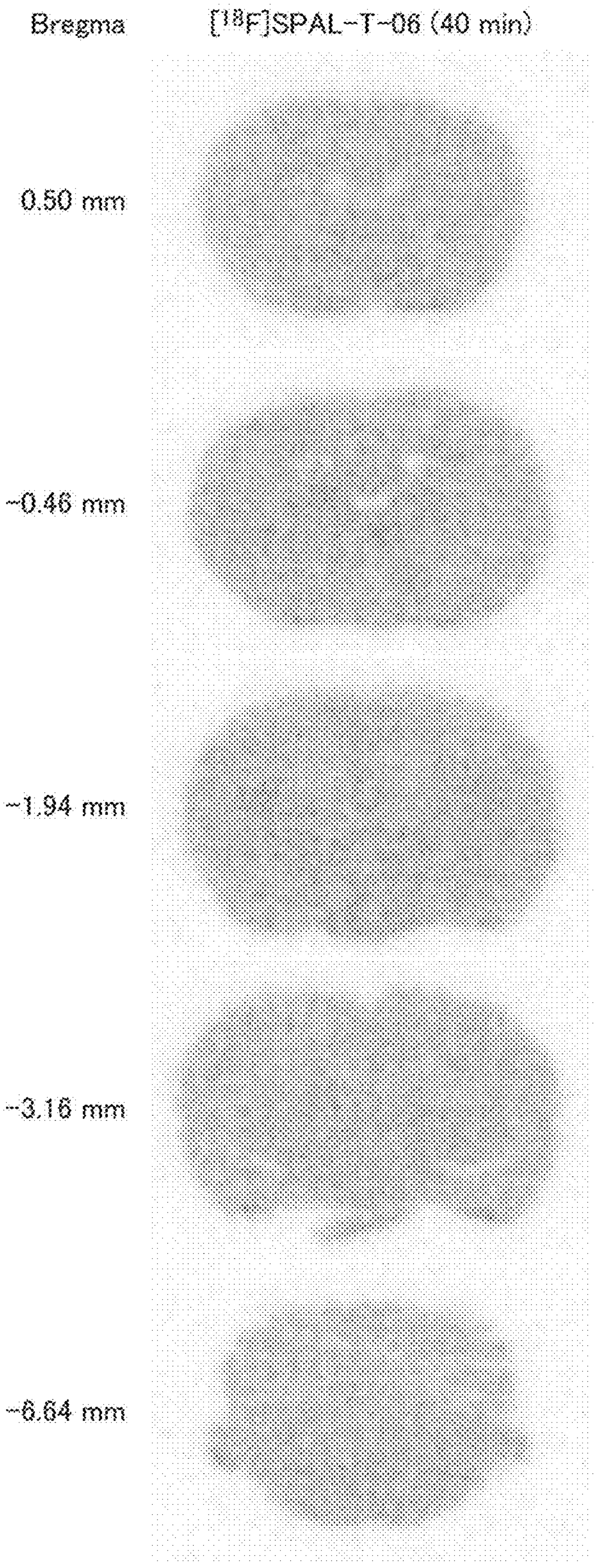
FIG. 8 is a diagram showing results of ex vivo imaging of a mouse brain.

It was found, from the results shown in FIG. 8, that even when [$^{18}$F]SPAL-T-06 was intravenously injected into the physiological saline-injected mouse, nonspecific accumulation of the compound delivered into the brain was not seen in the white matter area.

[Positron Emission Tomography (PET) Imaging of Marmoset Brain]

(Preparation of α-Synuclein Fibril-Inoculated Marmoset Model)

First, marmoset α-synuclein was expressed in and extracted from *E. coli* as a recombinant protein, and then incubated in vitro to form insoluble α-synuclein aggregates. The α-synuclein aggregates were then inoculated into the caudate nucleus and the putamen of the marmoset. The α-synuclein aggregates propagated to surrounding areas via the neural circuitry, and α-synuclein lesions were observed in the substantia nigra several months later. The inoculation of the α-synuclein aggregates into the caudate nucleus and the putamen of the marmoset was carried out in the following manner. First, an endotracheal tube was inserted into the marmoset immobilized with ketamine (5 mg/kg to 10 mg/kg) and xylazine (0.2 mg/kg to 0.5 mg/kg), and then the marmoset was anesthetized with 1% to 3% (v/v) isoflurane. Then, hair on the head of the marmoset was removed, and the scalp was disinfected with isodine, followed by application of xylocaine and incision in the scalp to expose the skull. A hole (a diameter of approximately 3 mm) was drilled in the skull at a position of 9.75 mm from the interaural line, and 50 μl of an α-synuclein fibril solution (marmoset α-synuclein fibril (4 mg/ml) in saline) was injected into each of the caudate nucleus and the putamen in the right hemisphere with use of a Hamilton's syringe. Furthermore, 50 μl of physiological saline was injected into each of the caudate nucleus and the putamen in the left hemisphere in a similar manner. Thereafter, the scalp was returned and sutured.

[In Vivo Positron Emission Tomography (PET) Imaging of Marmoset Brain]

Figure 9:
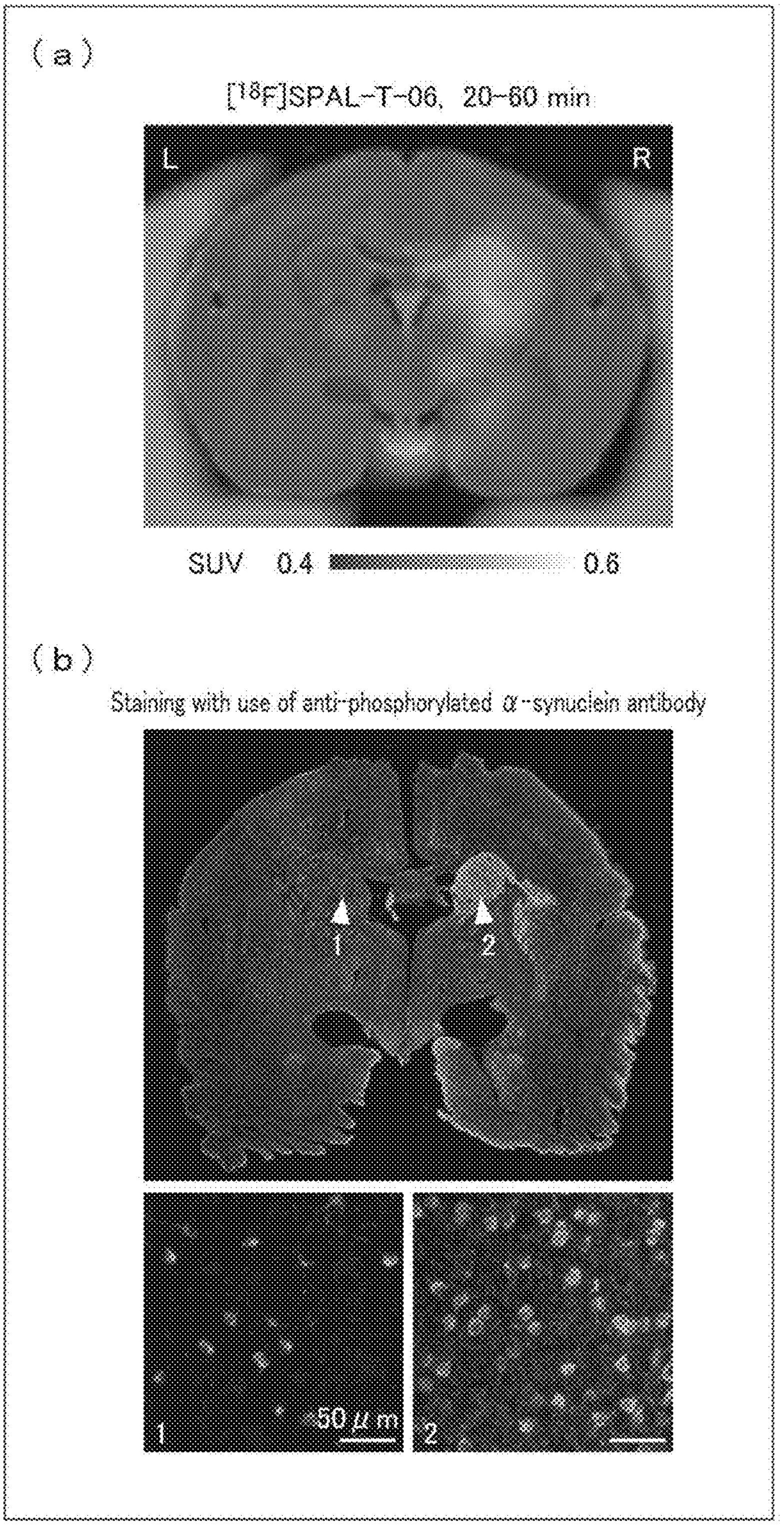
FIG. 9 is a diagram showing results of PET imaging of an α-synuclein fibril-inoculated marmoset.

PET scanning was carried out with use of a micro PET Focus 220 animal scanner (Siemens Medical Solutions), which provided 95 slices each having a thickness of 0.851 mm (center thickness), a 19.0-cm axial field of view (FOV) and a 7.6-cm cross-sectional FOV. Before the scanning, the α-synuclein fibril-inoculated marmoset was anesthetized with 1% to 3% (v/v) isoflurane. Transmission scanning was carried out with use of a PET calibration source Ge-68 for 20 minutes. Emission scanning was carried out in 3D list mode with an energy window of 350 keV to 750 keV for 90 minutes, after intravenous injection of [$^{18}$F]SPAL-T-06 (compound in which SPAL-T-06 was labeled with a positron-emitting radionuclide) (73.0 MBq). The injection of the radioactive compound and the scanning were carried out under dim light so as to avoid photoisomerization of the compound. The entire list mode data was sorted into 3D sinograms, and then converted into 2D sinograms by Fourier-rebining (frame: 10×1, 6×5, and 5×10 minutes). After the injection of the radioactive compound, summation images during time periods from 0 to 30 minutes, from 30 to 60 minutes, and from 60 to 90 minutes were obtained by maximum a posteriori reconstruction. Moreover, dynamic images were reconstructed by filtered back projection with use of a 0.5-mm Hanning filter. A result is shown in FIG. 9. (a) of FIG. 9 shows an image of a coronal section of the brain of the α-synuclein fibril-inoculated marmoset which includes the caudate nucleus, 20 minutes to 60 minutes after the intravenous injection of [$^{18}$F]SPAL-T-06. The image is superimposed on a standard brain MRI image.

(In Vitro Fluorescence Microscope Measurement)

The brain of the α-synuclein fibril-inoculated marmoset was extracted, and then a section was prepared. The section was analyzed by immunohistochemical staining. Specifically, the brain section of the α-synuclein fibril-inoculated marmoset was washed with a phosphate buffer solution, and then treated in an autoclave for antigen retrieval. After the section was subjected to immunohistochemical staining with use of an anti-phosphorylated α-synuclein monoclonal antibody (pS129, abcam, ab59264) (1:1000) and then mounted in a mounting medium (VECTASHIELD H-1000), images were obtained with use of fluorescence microscopes (BZ-X710, KEYENCE (excitation wavelength: 450 nm to 490 nm) and DM4000 (excitation wavelength: 460 nm to 500 nm)). A result is shown in FIG. 9. (b) of FIG. 9 shows an image of antibody staining, using anti-phosphorylated α-synuclein antibody, of the coronal section of the brain including the caudate nucleus obtained from of the α-synuclein fibril-inoculated marmoset. In (b) of FIG. 9, 2 shows an enlarged image of the caudate nucleus in the right hemisphere to which the α-synuclein fibril was inoculated and which was stained with anti-phosphorylated α-synuclein antibody, and 1 shows an enlarged image of the caudate nucleus in the left hemisphere to which the physiological saline was injected and which was stained with anti-phosphorylated α-synuclein antibody.

By carrying out PET scanning of the α-synuclein fibril-inoculated model marmoset into which SPAL-T-06 labeled with a positron-emitting radionuclide was intravenously injected, clear accumulation of [$^{18}$F]SPAL-T-06 in the caudate nucleus, which was rich in α-synuclein lesions, was observed. Thus, it was found that PET scanning with use of [$^{18}$F]SPAL-T-06 enabled imaging of α-synuclein aggregates.

[In Vitro Biding Test of Human Brain]

Figure 10:
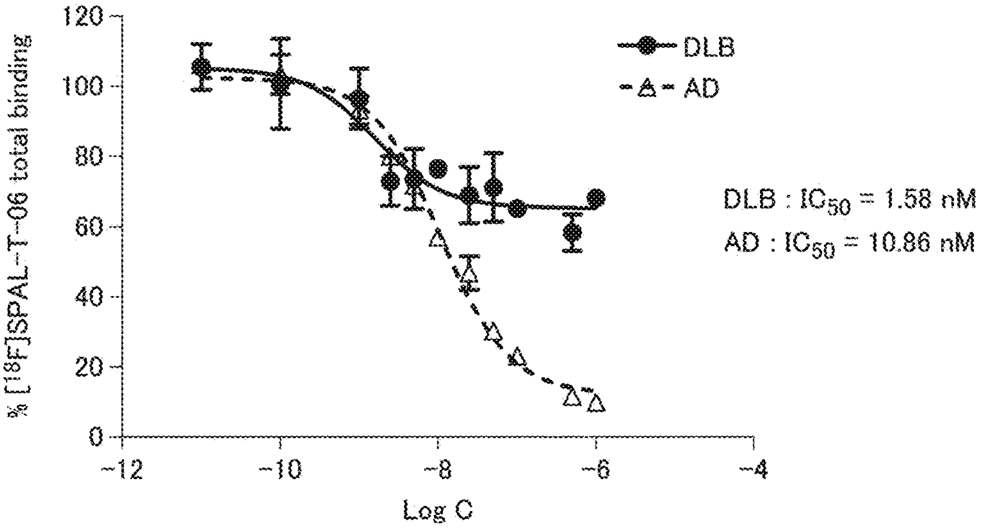
FIG. 10 is a diagram showing results of an in vitro biding test of the brains of DLB and AD patients.

Fresh frozen tissue from the amygdala in the brain of a DLB patient and fresh frozen tissue from the frontal cortex in the brain of an AD patient were used. To each fresh frozen brain tissue, zirconia beads (ZB-20, TOMY) and a buffer solution which was 10 times the wet weight of the tissue were added. A mixture thus obtained was smashed with use of Micro Smash (MS-100R, TOMY) and then stored at −80° C. A homogenate of the brain of the DLB patient or a homogenate of the brain of the AD patient, [$^{18}$F]SPAL-T-06 (final concentration: 5 nM), and non-labeled SPAL-T-06 (final concentration: 0.01 nM to 1 μM) were mixed into a Tris-HCl buffer solution (containing 20% ethanol). Incubation was carried out at room temperature for 30 minutes, and then B/F separation (B: bound ligand, F: free ligand) was carried out by suction filtration and washing. Thereafter, radioactivity captured on a glass filter was measured with use of a gamma counter (2480WIZARD2, ParkinElmer). With regard to the concentration of each non-labeled SPAL-T-06, a test was carried out in triplicate. Results were analyzed with use of Prism 6J (GraphPad), displacement curves of the tested compounds were obtained, and then $IC_{50}$ of each was calculated. Results are shown in FIG. 10.

As a result of binding tests with SPAL-T-06 labeled with a positron-emitting radionuclide and the homogenate of the brain of the DLB patient and the homogenate of the brain of the AD patient, it was found that [$^{18}$F]SPAL-T-06 bound, with high affinity, to the homogenate of the brain of the DLB patient which was rich in α-synuclein lesions ($IC_{50}$=1.58 nM). It was found that the binding affinity of [$^{18}$F]SPAL-T-06 with respect to the homogenate of the brain of the AD patient was lower ($IC_{50}$=10.86 nM) than that of [$^{18}$F]SPAL-T-06 with respect to the homogenate of the brain of the DLB patient, that [$^{18}$F]SPAL-T-06 exhibited favorable binding affinity as a probe for imaging α-synuclein aggregates in PET imaging, and that binding of [$^{18}$F]SPAL-T-06 to α-synuclein aggregates was stronger than to tau aggregates or amyloid B aggregates and thus had high binding selectivity with respect to α-synuclein aggregates.

[In Vitro Autoradiography of Human Brain]

(Dissected Brain Tissue)

Postmortem human brains were obtained in autopsies carried out with respect to a DLB patient, a multiple system atrophy (MSA) patient, and a healthy subject. In a cryostat (HM560, Carl Zeiss), frozen tissue from the DLB patient and frozen tissue from the healthy subject were sliced into sections each having a thickness of 20 μm. Brain tissue from the MSA patient was fixed in 10% neutral buffered formalin, embedded in a paraffin block, and sliced into sections each having a thickness of 6 μm.

(Autoradiography Test)

Figure 11:
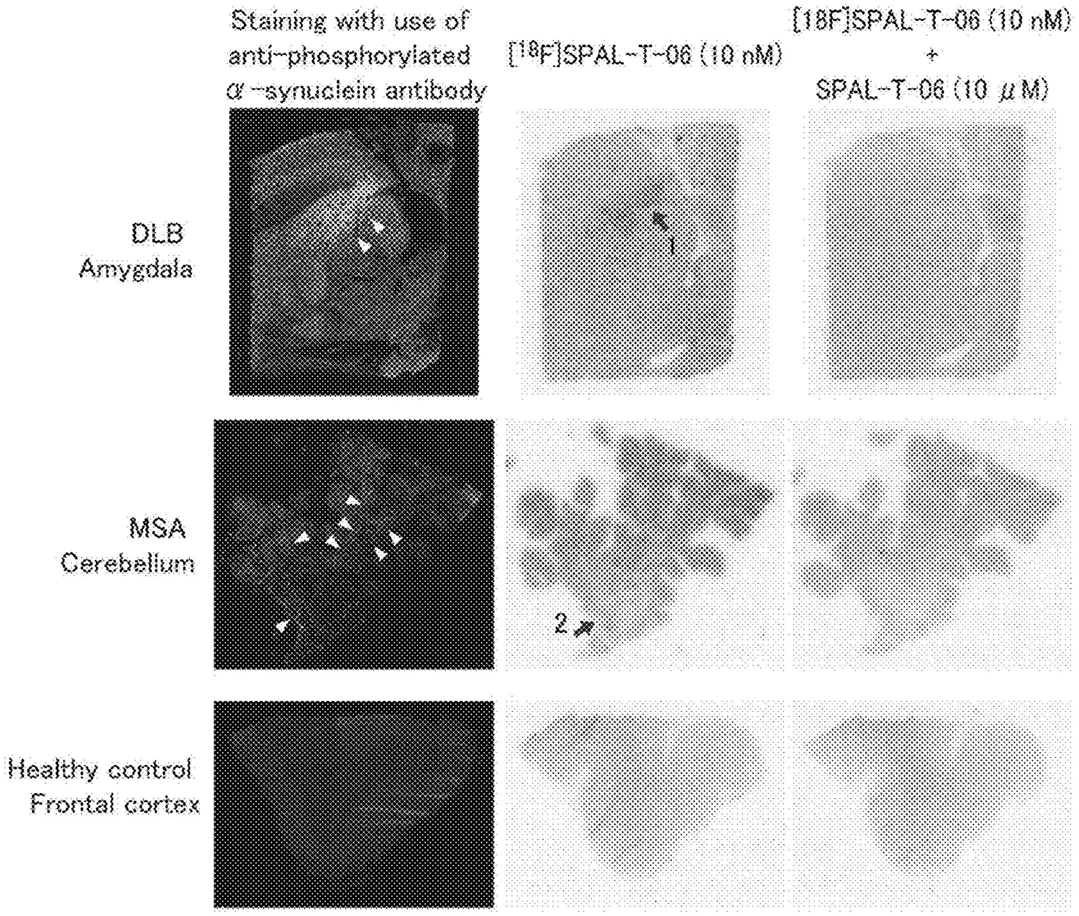
FIG. 11 is a diagram showing results of autoradiography of the brains of DLB and MSA patients.

Postfixed fresh frozen sections of amygdala tissue from the brain of the DLB patient and the frontal cortex tissue from the brain of the healthy subject and deparaffinized sections of formalin-fixed paraffin-embedded cerebellum tissue from the brain of the MSA patient were used. Each brain tissue section and [$^{18}$F]SPAL-T-06 (final concentration: 10 nM) were incubated in 50 mM Tris-HCl containing 20% ethanol at room temperature for 1 hour. In order to detect specific binding, the brain tissue section was also incubated in 50 mM Tris-HCl (containing 20% ethanol) containing [$^{18}$F]SPAL-T-06 (final concentration: 10 nM) and non-labeled SPAL-T-06 (final concentration: 10 μM). Subsequently, the section was washed with 50 mM Tris-HCl (containing 20% EtOH) at 4° C. for 2 minutes. This washing was carried out twice. Thereafter, the section was rinsed with MilliQ. The section was air-dried, and then placed in contact with an imaging plate for 5 minutes in a cassette. Thereafter, an autoradiograph was obtained with use of BAS-5000 (Fuji Film). Results are shown in FIG. 11. In FIG. 11, each arrowhead indicates an area in each of the brains of the DLB patient and the MSA patient which includes a lesion caused by phosphorylated α-synuclein.

(In Vitro Fluorescence Microscope Measurement)

Figure 12:
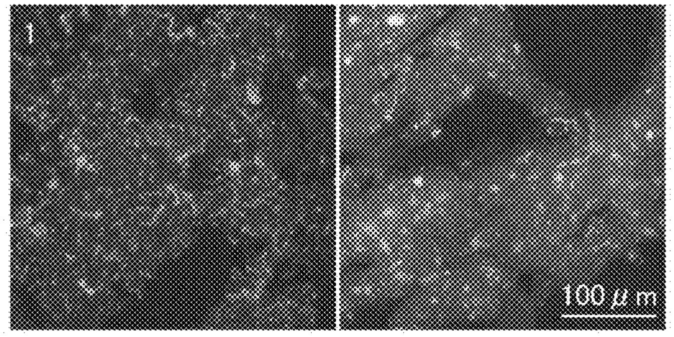
FIG. 12 is a diagram showing results of an in vitro fluorescence microscope measurement of the brains of DLB and MSA patients.
Figure 12:
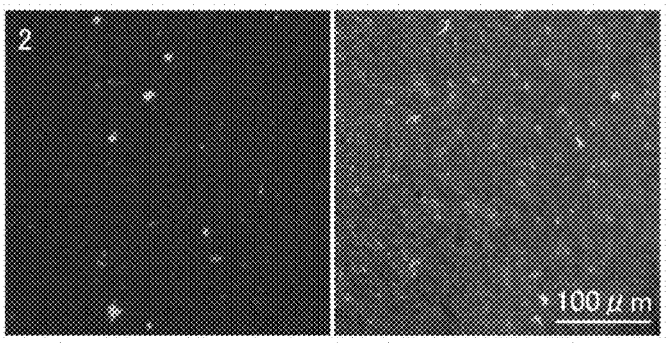

The section that had been subjected to the autoradiography was analyzed by fluorescent staining. Specifically, the section and 30 μM SPAL-T-06 were incubated in a 50% ethanol solution at room temperature for 30 minutes. Thereafter, the section was washed with a 50% ethanol solution for 5 minutes and with ultrapure water for 3 minutes. This washing was carried out twice. After the section was mounted in a mounting medium (VECTASHIELD H-1000), an image of an α-synuclein aggregate-enriched area on the section was obtained with use of a fluorescence microscope (DM4000 (excitation wavelength: 391 nm to 437 nm)). An adjacent brain section was also washed with a phosphate buffer solution, and then treated in an autoclave for antigen retrieval. After the section was subjected to immunohistochemical staining with an anti-phosphorylated α-synuclein monoclonal antibody (pS129, abcam, ab59264) (1:1000) and then mounted in a mounting medium (VECTASHIELD H-1000), images were obtained with use of fluorescence microscopes (BZ-X710, KEYENCE (excitation wavelength: 450 nm to 490 nm) and DM4000 (excitation wavelength: 460 nm to 500 nm)). Results are shown in FIG. 12. (a) (indicated by "1") of FIG. 12 shows the brain of the DLB patient which has been subjected to staining with use of the anti-phosphorylated α-synuclein antibody and fluorescent staining by SPAL-T-06. (b) (indicated by "2") of FIG. 12 shows the brain of the MSA patient which has been subjected to staining with use of the anti-phosphorylated α-synuclein antibody and fluorescent staining by SPAL-T-06.

As a result of autoradiography of a section of the amygdala in the brain of the DLB patient, a section of the cerebellum in the brain of the MSA patient, and a section of the frontal cortex in the brain of the healthy subject using SPAL-T-06 labeled with a positron-emitting radionuclide, it was found that [$^{18}$F]SPAL-T-06 bound to areas in the brains of the DLB patient and the MSA patient which were rich in lesions caused by phosphorylated α-synuclein. As a result of fluorescent staining and immunohistochemical staining of the sections that had been subjected to the autoradiography, it was found that SPAL-T-06 bound to α-synuclein lesions included in these brain sections. In the section of the frontal cortex in the brain of the healthy subject, non-specific binding of [$^{18}$F]SPAL-T-06 was hardly observed in both of the gray matter and the white matter.

INDUSTRIAL APPLICABILITY

According to the present invention, it is possible to provide an α-synuclein aggregate binding agent having high binding selectivity with respect to α-synuclein aggregates. Furthermore, it is possible to provide a method for carrying out imaging with use of this α-synuclein aggregate binding agent. Moreover, it is possible to provide a novel compound which can be used for the α-synuclein aggregate binding agent or the other applications.

The invention claimed is:

1. A compound represented by the following formula (I) or (II), a pharmaceutically acceptable salt thereof, or a solvate thereof (I)

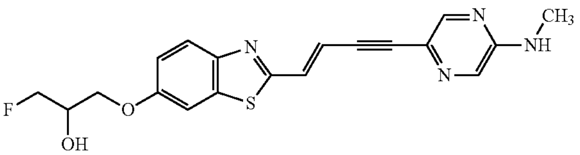

(II)

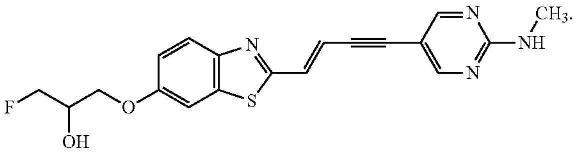

2. The compound, the pharmaceutically acceptable salt thereof, or the solvate thereof as set forth in claim 1, wherein one or more atoms in the compound represented by the formula (I) or (II) are radioisotopes thereof.

3. An α-synuclein aggregate binding agent comprising a compound, a pharmaceutically acceptable salt, or a solvate thereof recited in claim 1.

4. An α-synuclein aggregate binding agent comprising a compound, a pharmaceutically acceptable salt, or a solvate thereof recited in claim 2.

5. A composition for optical imaging of α-synuclein aggregates, said composition comprising an α-synuclein aggregate binding agent recited in claim 3.

6. A composition for radiological imaging of α-synuclein aggregates, said composition comprising an α-synuclein aggregate binding agent recited in claim 4.

7. A method for carrying out optical imaging of α-synuclein aggregates in brain, said method comprising a step of detecting light which has a second wavelength and which is emitted from the brain of a living subject, after externally irradiating the brain with light which has a first wavelength, wherein an α-synuclein aggregate binding agent recited in claim 3 has been administered to the living subject, and the first wavelength and the second wavelength are different from each other.

8. A method for carrying out radiological imaging of α-synuclein aggregates in brain, said method comprising a step of detecting radioactivity which is emitted from the brain of a living subject to which an α-synuclein aggregate binding agent recited in claim 4 has been administered.

9. An intermediate for synthesizing the compound recited in claim 1, the intermediate being represented by the following formula (III):

(III)

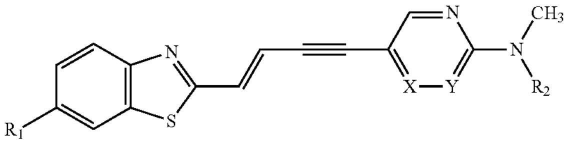

wherein:

one of X and Y is a nitrogen atom (N), and the other is an unsubstituted carbon atom (CH);

$R_1$ is a hydroxy group or a group represented by the following formula (i):

(i)

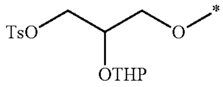

wherein Ts represents a p-toluenesulfonyl group,

THP represents a tetrahydro-2H-pyran-2-yl group, and

* represents a position to which a benzothiazole ring binds; and $R_2$ is a hydrogen atom or a tert-butoxycarbonyl (Boc) group.

10. An intermediate for synthesizing the compound recited in claim 2, the intermediate being represented by the following formula (III):

(III)

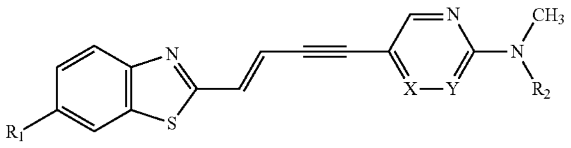

wherein:

one of X and Y is a nitrogen atom (N), and the other is an unsubstituted carbon atom (CH);

$R_1$ is a hydroxy group or a group represented by the following formula (i):

(i)

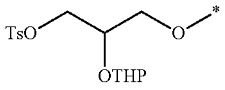

wherein Ts represents a p-toluenesulfonyl group,

THP represents a tetrahydro-2H-pyran-2-yl group, and

* represents a position to which a benzothiazole ring binds; and $R_2$ is a hydrogen atom or a tert-butoxycarbonyl (Boc) group.

* * * * *